US009873667B2

(12) United States Patent
Pusztay et al.

(10) Patent No.: US 9,873,667 B2
(45) Date of Patent: Jan. 23, 2018

(54) ARYLSULFANYL COMPOUNDS AND COMPOSITIONS FOR DELIVERING ACTIVE AGENTS

(75) Inventors: Stephen Pusztay, Ansonia, CT (US); Sushma Saraf, Wappingers Falls, NY (US); Nai Fang Wang, Scarsdale, NY (US)

(73) Assignee: EMISPHERE TECHNOLOGIES INC., Roseland, NJ (US)

( * ) Notice: Subject to any disclaimer, the term of this patent is extended or adjusted under 35 U.S.C. 154(b) by 626 days.

(21) Appl. No.: 12/375,369

(22) PCT Filed: Jul. 27, 2007

(86) PCT No.: PCT/US2007/074534
§ 371 (c)(1),
(2), (4) Date: Feb. 5, 2009

(87) PCT Pub. No.: WO2008/014430
PCT Pub. Date: Jan. 31, 2008

(65) Prior Publication Data
US 2009/0258817 A1 Oct. 15, 2009

Related U.S. Application Data

(60) Provisional application No. 60/280,572, filed on Jul. 27, 2006.

(51) Int. Cl.
*A61K 38/28* (2006.01)
*A61K 31/192* (2006.01)
*A61K 38/16* (2006.01)
*A61P 3/10* (2006.01)
*C07C 323/52* (2006.01)
*C07C 323/62* (2006.01)
*A61K 47/20* (2006.01)
*C07C 323/56* (2006.01)

(52) U.S. Cl.
CPC ............ *C07C 323/52* (2013.01); *A61K 47/20* (2013.01); *C07C 323/56* (2013.01); *C07C 323/62* (2013.01)

(58) Field of Classification Search
CPC combination set(s) only.
See application file for complete search history.

(56) References Cited

U.S. PATENT DOCUMENTS

| 3,024,248 | A | 3/1962 | Werner |
| 6,300,514 | B1 | 10/2001 | Takahashi et al. |
| 6,627,651 | B1 | 9/2003 | Shiraishi et al. |
| 6,808,854 | B2 | 10/2004 | Imamura et al. |
| 2005/0288329 | A1 | 12/2005 | Yao et al. |

FOREIGN PATENT DOCUMENTS

| CA | 2343151 A1 | 3/2000 |
| DE | 3339644 A1 | 5/1984 |
| EP | 0841339 A1 | 5/1998 |
| EP | 1 452 605 A1 * | 9/2004 |
| WO | WO 96/27369 * | 9/1996 |
| WO | WO-9804290 A2 | 2/1998 |
| WO | WO-9805635 A1 | 2/1998 |
| WO | WO-9829382 A1 | 7/1998 |
| WO | WO-9940883 A2 | 8/1999 |
| WO | WO 00/01692 A1 | 1/2000 |
| WO | WO-0007979 A2 | 2/2000 |
| WO | WO-0102379 A1 | 1/2001 |
| WO | WO-03057161 A2 | 7/2003 |
| WO | WO-03059875 A2 | 7/2003 |
| WO | WO-03062369 A2 | 7/2003 |

OTHER PUBLICATIONS

Silverman (The Organic Chemistry of Drug Design and Drug Action, 1992, pp. 15-20).*
Amino et al: "Phenylalanine derivatives enhancing intestinal absorption of insulin in mice", Chemical and Pharmaceutical Bulletin, Pharmaceutical Society of Japan, Tokyo, JP, vol. 36, No. 11, Jan. 1, 1988 (Jan. 1, 1988), pp. 4426-4434, XP002257551, ISSN: 0009-2363.
Chen S-L et al: "Synthesis, DNA cleavage and cytotoxicity of some novel cyclic peptide-2,6-dimethoxy-hydroquinone-3-mercaptoacetic acid conjugates containing D-amino acids", Anti-Cancer Drug Design, Oxford University Press, Bas Ingstoke, vol. 13, Jan. 1, 1998 (Jan. 1, 1998), pp. 501-518, XP009147494, ISSN: 0266-9536.
Chu Sae-Lee et al: "The Preparation of the Derivatives of 3-Dialkylaminomethyl Thiachroman-4-", Acta Chimica Sinica—Huaxue Xuebao, Science Press, Beijing, CN, vol. 22, Jan. 1, 1956 (Jan. 1, 1956), pp. 371-378, XP009078727, ISSN: 0256-7660.
Database Caplus [Online] Chemical Abstracts Service, Columbus, Ohio, US; Kuliev, A. M. et al: "Synthesis and study of 2,5-dialkylphenylthioacetic acids", retrieved from STN Database accession No. 1967:463972.
Database Caplus [Online] Chemical Abstracts Service, Columbus, Ohio, US; Gurumurthy. R. AL: "Kinetics and mechanism of oxidation of substituted S-", retrieved from STN Database accession No. 1998:470012.
Database Caplus [Online] Chemical Abstracts Service, Columbus, Ohio, US; Kukalenko, S. S.: "Organic insectofungicides. I. Synthesis and some reactions of .gamma.-arylthiobutyric acids", retrieved from STN Database accession No. 1970:414392.
Database Caplus [Online] Chemical Abstracts Service, Columbus, Ohio, US; Xiao, Li-Wei et al: "Synthesis of .beta.-arylthioethers of propionic acid and thiochromanones under microwave irradiation", retrieved from STN Database accession No. 2006:715347.
Database Caplus [Online] Chemical Abstracts Service, Columbus, Ohio, US; Gogia, Santosh et al: "Nickel chloride hexahydrate: A novel reagent for Michael addition on α,β-unsaturated acids—A facile one-step route to 3-arylmercaptopropionic acids from thiophenols and α,β-unsaturated acids", retrieved from STN Database accession No. 2004:813045.
Database Caplus [Online] Chemical Abstracts Service, Columbus, Ohio, US; Chu, Sae-Lee et al: "Thiachromanones. II. The preparation of 3-dialkylaminomethylthiachromanones. 2", retrieved from STN Database accession No. 1959:39911.

(Continued)

*Primary Examiner* — Rosalynd A Keys
(74) *Attorney, Agent, or Firm* — Blank Rome LLP

(57) ABSTRACT

Compounds and compositions for the delivery of active agents are provided. Methods of administration and preparation are also provided.

23 Claims, 7 Drawing Sheets

(56) References Cited

OTHER PUBLICATIONS

Database Caplus [Online] Chemical Abstracts Service, Columbus, Ohio, US; Kresze, Gunter et al: "Structure of organosulfur compounds. V. The kinetics of oxidation of some aryl sulfides and sulfoxides", retrieved from STN Database accession No. 1961 :137229.

Database Caplus [Online] Chemical Abstracts Service, Columbus, Ohio, US; Siatra-Papastaicoudi, T. et al: "ω-Alkylaminoethyl esters of phenylthioisobutyric acid. Chemistry and pharmacodynamic activity", retrieved from STN Database accession No. 91 :91312 ; & Chimika Chronika , 8(1), 3-8 Coden: CMCRCZ; ISSN: 0366-693X, 1979.

Donald P Gowing and Robert W Leeper: "Relation of chemical structure to plant growth-regulator activity in the pineapple plant. II. Compounds related to phenoxyalkylcarboxylic acids, phthalamic acids, and benzoic acids", Botanical Gazette, SN, Hanover, IN, US, vol. 121, No. 4, Jun. 1, 1960 (Jun. 1, 1960), pp. 249-257, XP009147541, ISSN: 0006-8074.

Donald P Gowing and Robert W Leeper: "Uncommon Plant Growth Regulators for the Control of Nutgrass and Oxalis", Weeds, Weed Society of America, Urbana, IL, US, vol. 8, Jan. 1, 1960 (Jan. 1, 1960), pp. 279-283, XP009147526, ISSN: 0096-719X.

E.A. Bartkus et al: "Synthesis and Properties of the Six Thioxylenol Isomers", J. Org. Chem., vol. 22, No. 10, 1957, pp. 1185-1186.

George Allen Gnanaraj et al: "Photoredox Reactions of Polypyridyl Chromium (III) Complexes with Arylthioacetic Acids in Acetonitrile and Aqueous Media", Tetrahedron, vol. 50, No. 31,1994, pp. 9447-9456.

Gogia, S. et al: "Nickel Chloride Catalyzed Arylation of 3-Mercaptopropionic Acid: A Facile One-Step Route to 3-Aryl Mercaptopropionic Acids from Unactivated Aryl Halides and Arenes.", rearm 1703 01.91TRI Cheminform, vol. 36, No. 12, Feb. 24, 2005 (Feb. 24, 2005), ; & Indian Chem. Soc., vol. 81, No. 6, 2004, pp. 515-517.

Gogia, S. et al: "Nickel Chloride Hexahydrate: A Novel Reagent for Michael Addition on alpha,beta-Unsaturated Acid—A Facile One Step Route to 3-Arylmercaptopropionic Acids from Thiophenols and alpha, beta Unsaturated Acids", Cheminform, vol. 35, no. 36, Aug. 11, 2004 (Aug. 11, 2004), ; & Indian J. Chem., Sect B: Org. Chem. Incl. Med. Chem., vol. 43, No. 5, 2004, pp. 1008-1011.

Gortner W A et al: "Studies on the Relation of Chemical Structure to Plant Growth-Regulator Activity in the Pineapple Plant. V. Post-Harvest Delay of Senescence of Pineapple Fruit", Botanical Gazette, SN, Hanover, IN, US, vol. 130, No. 2,Jan. 1, 1969 (Jan. 1, 1969), pp. 87-97, XP009030077, ISSN: 0006-8074, 001: 001:10. 1086/336474.

Jasjit S. Bindra et al: "Studies in Antifertility Agents. 8. Seco Steroids. 2. 5,6-Secoestradiol and Some Related Compounds", J. Med. Chem., vol. 18, No. 9, 1975, pp. 921-925.

Kucharczyk, N. et al: "Metabolism and pharmacokinetics of 4-(pchlorophenylthio)butanol (W-2719) in the rat and dog.", Arzneimittelforschung, vol. 29, No. 10, 1979, pp. 1550-1556.

Mary J Meegan et al: "Benzothiepin-derived molecular scaffolds for estrogen receptor modulators: synthesis and antagonistic effects in breast cancer cells", Journal of Enzyme Inhibition and Medicinal Chemistry, Taylor, Reading, GB, vol. 22, Jan. 1, 2007 (Jan. 1, 2007), pp. 655-666, XP009147525, ISSN: 1475-6366, 001: 001:10.1080/ 14756360701503232.

Pettit L 0 et al: "A comparison of the donor properties of group VIB elements", Journal of the Chemical Society, Chemical Communications, Chemical Society. Letchworth, GB, Jan. 1, 1967 (Jan. 1, 1967), pp. 1179-1180, XP009147536, ISSN: 0022-4936, 001: 001:10.1 039/C19670001179.

Sugii, Michiyasu & Sugii, Atsushi: "Studies on the Phytohormones. (I) : On the Growth Promoting Activity for Plants of Arylthioglycolic Acid Derivatives" , Bulletin of the Institute for Chemical Research, Kyoto University, vol. 31, No. 1, Jan. 30, 1953 (Jan. 30, 1953), pp. 27-33.

Thenraja D et al: "Kinetics and mechanism of oxygenation of aromatic sulfides and arylmercaptoacetic acids by peroxomonophosphoric acid", Tetrahedron, Elsevier Science Publishers, Amsterdam, NL, vol. 58, No. 21, May 20, 2002 (May 20, 2002), pp. 4283-4290, XP004357402, ISSN: 0040-4020, DOI: DOI:10.1016/S0040-4020(02)00358-7.

Ya-Wen Chiu et al: "A Monoclonal Immunoassay for the Coplanar Polychlorinated Biphenyls", Analytical Chemistry, American Chemical Society, US, vol. 67, No. 21, Nov. 1, 1995 (Nov. 1, 1995), pp. 3829-3839, XP000540823, ISSN: 0003-2700, DOI: DOI:10. 1021/AC00117A003.

Japanese Unexamined Patent Applicaiton, First Publication No. H08-127581, English Abstract prepared by the Japanese Patent Office, May 21, 1996, JP 08-127581.

Manimekalai, et al., Complexation Studies of Copper (II) with Some S-phenyl, Asian Journal of Chemistry, 1996, 8:2:193-196.

Baker, et al., Irreversible Enzyme Inhibitors, 195, Inhibitors of Thymidine Kinase from Walker 256 Carcinoma Derived from Thymidine 5'-Acetate, Journal of Medicinal Chemistry, 1972, 15:9:940-944.

Levkovskaya, et al., 2-Hydroxyalkylammonium Arylthioacetates and Their Effects on the Functional Activity of Thrombocytes, Pelnum Publishing Corporation, 1987, 180-184.

Tardy, et al, Topoisomerase I-mediated DNA Cleavage as a Guide to the Development of Antitumor agents derived from the Marine Alkaloid Lamellarin D:triester Derivatives Incorporating Amino Acid Residues, Bioorganic & Medicinal Chemistry, 2004, 12:1697-1712.

\* cited by examiner

**Caspofungin Acetate (ng/ml)
Oral Administration of Caspofungin Acetate in Rats**

ARYLSULFANYL COMPOUNDS AND COMPOSITIONS FOR DELIVERING ACTIVE AGENTS

CROSS-REFERENCE TO PRIOR APPLICATIONS

This is a U.S. National Phase Application under U.S.C. §371 of International Patent Application No. PCT/US2007/74534 filed Jul. 27, 2007, which claims the benefit of U.S. Provisional Application No. 60/820,572, filed Jul. 27, 2006. The International Application published in English on Jan. 31, 2008 as WO 2008/014430 under Article 21(2).

FIELD OF THE INVENTION

The present invention relates to pharmaceutical compounds for delivering active agents, such as biologically or chemically active agents, to a target. Methods for the preparation and administration of such compositions are also disclosed.

BACKGROUND OF THE INVENTION

Conventional means for delivering active agents are often severely limited by biological, chemical and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the formula:

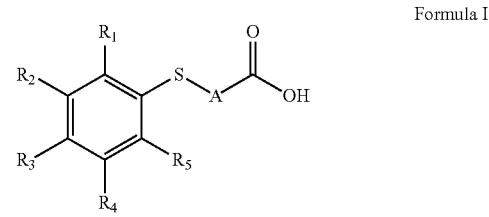

Formula I and pharmaceutically acceptable salts thereof, wherein
A is a branched or unbranched $C_1$-$C_{13}$ alkylene, $C_3$-$C_{13}$ arylene group, or a $C_3$-$C_{13}$ alkyl(arylene) group,
$R_1$-$R_5$ are independently a hydrogen, $C_1$-$C_4$ alkyl, $C_1$-$C_4$ alkoxy, $C_2$-$C_4$ alkenyl, halogen or hydroxy group.

According to one embodiment, delivery agent compounds include those represented by Formula I above, in which A is a $C_1$-$C_{12}$, or $C_1$-$C_{10}$, or $C_1$-$C_9$, or $C_1$-$C_8$, or $C_1$-$C_7$, or $C_2$-$C_7$, or $C_3$-$C_7$, or $C_4$-$C_7$ or $C_5$-$C_7$, or $C_6$-$C_7$ alkylene group; and/or at least one of $R_1$ to $R_5$ is a methyl, methoxy, hydroxy or halogen group (e.g., Cl or F).

In a preferred embodiment, A, as defined above in Formula I, is an unsubstituted and unbranched, i.e. straight-chained, alkylene group.

Mixtures of these delivery agent compounds may also be used.

The invention also provides a pharmaceutical composition comprising at least one delivery agent compound of the present invention, and at least one active agent (e.g. a biologically active agent). When administered with an active agent, delivery agents of the present application improve the bioavailability of the active agent compared to administration of the active agent without the delivery agent compound.

Also provided is a dosage unit form comprising a pharmaceutical composition of the present invention. The dosage unit form may be in the form of a liquid or a solid, such as a tablet, capsule or particle, including a powder or sachet.

Another embodiment is a method for administering an active agent to an animal, particularly an animal in need of the active agent, by administering a pharmaceutical composition comprising at least one of delivery agent compound of the present invention and the active agent to the animal. Preferred routes of administration include the oral and intracolonic routes, particularly the oral route.

Yet another embodiment of the present invention is a method of treating a disease or for achieving a desired physiological effect in an animal (e.g. a human) by administering to the animal the pharmaceutical composition of the present invention.

Yet another embodiment of the present invention is a method of preparing a pharmaceutical composition of the present invention by mixing at least one delivery agent compound of the present invention, and at least one active agent.

Yet another embodiment of the present invention is a method of increasing the bioavailability (e.g., the oral bioavailability) of a pharmaceutical composition containing an active agent (e.g., a biologically active agent) comprising adding a delivery agent compound of the present invention to the pharmaceutical composition.

DETAILED DESCRIPTION OF THE INVENTION

Definitions

Figure 1:
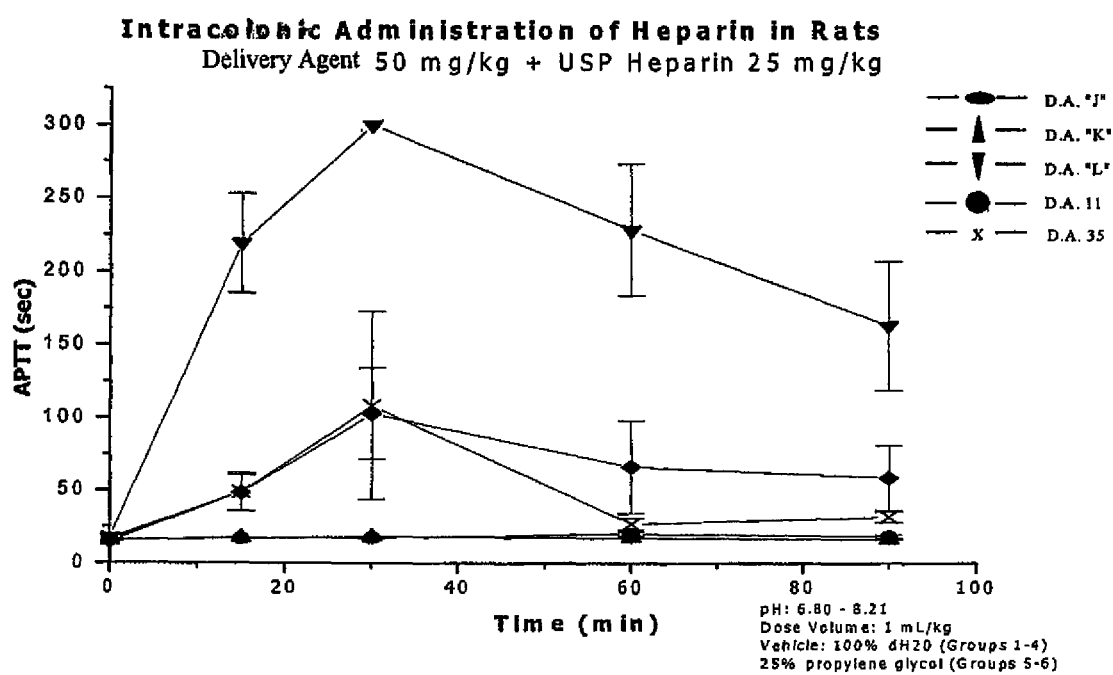
FIGS. 1 and 2 are graphs of aPTT times obtained after administration of heparin with delivery agents 1, 11, 35 and 59 to male rats over 90 minutes.

The term "alkyl" refers to a straight-chained, branched, or substituted monovalent aliphatic hydrocarbon group containing no double or triple carbon-carbon bonds. Examples of alkyl group include, but are not limited to, methyl, ethyl, n-propyl, 1-methylethyl(isopropyl), n-butyl, n-pentyl, and 1-dimethylethyl(t-butyl).

The term "alkenyl" refers to a straight-chained, branched, or substituted monovalent aliphatic hydrocarbon group containing at least one carbon-carbon double bond. Examples of alkenyl groups include, but are not limited to, ethenyl, 1-propenyl, 2-propenyl (allyl), iso-propenyl, 2-methyl-1-propenyl, 1-butenyl, and 2-butenyl.

The term "alkynyl" refers to a straight-chained, branched or substituted monovalent hydrocarbon group having at least one carbon-carbon triple bond. Examples of alkynyl groups include, but are not limited to ethynyl, propynyl, and butynyl.

The term "alkylene" refers to a straight-chained, branched or substituted divalent aliphatic hydrocarbon group containing no double or triple bonds.

The term "alkenylene" refers to a straight-chained, branched or substituted divalent aliphatic hydrocarbon group containing at least one carbon-carbon double bond.

The term "alkynylene" refers to a straight-chained or branched divalent aliphatic hydrocarbon group containing at least one carbon-carbon triple bond.

The term "alkyloxy" refers to an alkyl group attached via an oxygen linkage to the rest of the molecule. Examples of alkyloxy groups include, but are not limited to, $-OCH_3$, and $-OC_2H_5$ groups.

The term "aryl" refers to an monovalent aromatic group, i.e. a monovalent group having one or more unsaturated carbon rings. Examples of aryl groups, include, but are not limited to, phenyl, naphthyl, tetrahydronaphthyl, indanyl, and biphenyl.

The term "arylene" refers to a divalent aromatic group, i.e. a divalent group having one or more unsaturated carbon rings.

The term "alkyl(arylene)" refers to a divalent group containing an aromatic group with an alkyl group before and/or after the aromatic group.

The term "aryloxy" refers to an aryl group attached via an oxygen linkage to the rest of the molecule, such as $-OC_6H_5$.

The term "insulin" includes recombinant forms of insulin (e.g. recombinant human insulin), analogs of insulin lispro or Humalog®) as well as regular forms of insulin of human or other animal origin.

The term "heparin" includes unfractionated heparin, low molecular weight heparin, very low molecular weight heparin, of recombinant, human, or other animal origin.

The term "LHRH" or "luteinizing hormone-releasing hormone" refers to a hormone produced by the hypothalamus that signals the anterior pituitary gland to begin secreting luteinizing hormone and follicle-stimulating hormone.

The term "rhGH" refers to recombinant human growth hormone.

The term "caspofungin" or "caspofungin acetate" refers to a water-soluble, semisynthetic lipopeptide derived from the fungus, *Glarea lozoyensis*, that has activity against *Aspergilllus* and *Candida* species. Caspofugin acetate (Cancidas®) has been approved by the FDA and is indicated for the treatment of invasive aspergillosis in patients who are refractory to or intolerant of other antifungal agents.

Unless otherwise specified, the term "substituted" as used herein refers to substitution with any one or any combination of the following substituents: hydroxy, $C_1$-$C_4$ alkyl, including methyl, ethyl, propyl, isopropyl, normal or iso-butyl; aryl, alkoxy, or aryloxy groups.

The term "multiply interrupted" refers to between 2 and 10 interruptions in a chain where each interruption can be independently before, after, or between any other bond along the chain and may occur in any order or combination.

The term "about" means generally means within 10%, preferably within 5%, and more preferably within 1% of a given range.

The term "short stature" refers to a subject with a size (e.g. a height) that is significantly below what is considered normal. Growth hormone, e.g., human growth hormone, is indicated for short stature.

Delivery Agent Compounds

Delivery agent compounds of the present invention include those compounds represented by Formula I below, and pharmaceutically acceptable salts thereof:

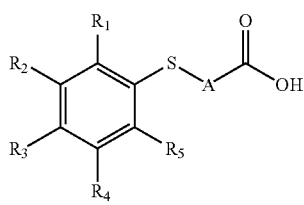

Formula I wherein

A is a branched or unbranched $C_1$-$C_{13}$ alkylene, $C_3$-$C_{13}$ arylene group, or a $C_3$-$C_{13}$ alkyl(arylene) group, $R_1$-$R_5$ are independently a hydrogen, $C_1$-$C_4$ alkyl, $C_1$-$C_4$ alkoxy, $C_2$-$C_4$ alkenyl, halogen or hydroxy group.

In one embodiment delivery agents of the present invention include those compounds represented by Formula I above, wherein A is a $C_1$-$C_9$ alkylene group, a $C_2$-$C_9$ alkylene group, a $C_3$-$C_9$ alkylene group, a $C_4$-$C_9$ alkylene group, a $C_5$-$C_9$ alkylene group, a $C_6$-$C_9$ alkylene group, a $C_7$-$C_9$ alkylene group, a $C_8$-$C_9$ alkylene group, a $C_2$-$C_8$ alkylene group, a $C_3$-$C_8$ alkylene group, a $C_4$-$C_8$ alkylene group, a $C_5$-$C_8$ alkylene group, a $C_6$-$C_8$ alkylene group, a $C_7$-$C_8$ alkylene group, a $C_3$-$C_7$ alkylene group, a $C_4$-$C_7$ alkylene group, a $C_5$-$C_7$ alkylene group, a $C_6$-$C_7$ alkylene group, a $C_7$ alkylene group, a $C_8$ alkylene group, or a $C_9$ alkylene group.

In another embodiment delivery agents of the present invention include those compounds represented by Formula I above, wherein A is selected from:

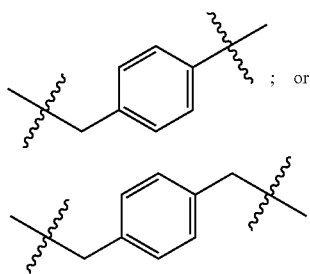

In another embodiment of the present invention, delivery agent compounds of the present invention include those compounds represented by Formula I above in which at least one of $R_1$-$R_5$ is a methyl, methoxy, hydroxy or halogen group. In a preferred embodiment, delivery agent compounds include those in which A is defined as in the preceding paragraph and at least one of $R_1$-$R_5$ is a methyl, methoxy, hydroxy or halogen group.

In one embodiment of the present invention, delivery agent compounds are selected from Formula I above, in which at least one of $R_1$-$R_5$ is a methyl group. In another embodiment, delivery agent compounds are selected from Formula I above in which at least one of $R_1$-$R_5$ is a methoxy group. In another embodiment, delivery agent compounds are selected from Formula I above in which at least one of $R_1$-$R_5$ is a hydroxy group. In another embodiment, delivery agent compounds are selected from Formula I above in which at least one of $R_1$-$R_5$ is a halogen, preferably at least one of $R_1$-$R_5$ is a chlorine atom or at least one of $R_1$-$R_5$ is a fluorine atom.

In one embodiment of the present invention, 3,4-dichlorophenylsulfanyl acetic acid is excluded as a delivery agent of Formula I. However, in various embodiments 3,4-dichlorophenylsulfanyl acetic acid may be included in compositions that further include an active agent (e.g., a biologically active agent).

In one embodiment of the present invention, delivery agent compounds include those represented by Formula II below, and pharmaceutically acceptable salts thereof:

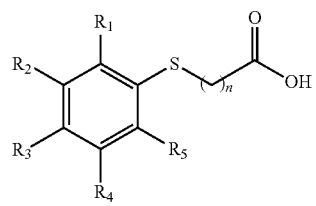

Formula II wherein n=1 to 9, and $R_1$-$R_5$ are independently hydrogen, $C_1$-$C_4$ alkyl, $C_1$-$C_4$ alkoxy, $C_2$-$C_4$ alkenyl, halogen or hydroxy with the proviso that when n=1, $R_2$ and $R_3$ are not both chlorine.

In one embodiment of the present invention, delivery agent compounds include compounds represented by Formula II above, in which n is 1, 2, 3, 4, 5, 6, 7, 8 or 9. Alternatively, n may be 1-9, 2-9, 3-9, 4-9, 5-9, 6-9, 7-9, 8-9, 1-8, 2-8, 3-8, 4-8, 5-8, 6-8, 7-8, 1-7, 2-7, 3-7, 4-7, 5-7, 6-7, 1-6, 2-6, 3-6, 4-6, 5-6, 1-5, 2-5, 3-5, 4-5, 1-4, 2-4, 3-4, 1-3, 2-3 or 1-2.

In another embodiment of the present invention, delivery agent compounds include compounds represented by Formula II above, in which at least one of $R_1$-$R_5$ is a methyl, methoxy, hydroxy or halogen group. In one embodiment of the present invention, delivery agent compounds are selected from Formula II above, in which at least one of $R_1$-$R_5$ is a methyl group. In another embodiment, delivery agent compounds are selected from Formula II above in which at least one of $R_1$-$R_5$ is a methoxy group. In another embodiment, delivery agent compounds are selected from Formula II above in which at least one of $R_1$-$R_5$ is a hydroxy group. In another embodiment, delivery agent compounds are selected from Formula II above in which at least one of $R_1$-$R_5$ is a halogen, preferably at least one of $R_1$-$R_5$ is a chlorine atom or at least one of $R_1$-$R_5$ is a fluorine atom.

In one embodiment of the present invention, 3,4-dichlorophenylsulfanyl acetic acid is excluded as a delivery agent of Formula II.

The delivery agent compounds may be in the form of the free base or pharmaceutically acceptable salts thereof, such as pharmaceutically acceptable acid addition salts. Suitable salts include, but are not limited to, organic and inorganic salts, for example ammonium, acetate salt, citrate salt, halide (preferably hydrochloride), hydroxide, sulfate, nitrate, phosphate, alkoxy, perchlorate, tetrafluoroborate, carboxylate, mesylate, fumerate, malonate, succinate, tartrate, acetate, gluconate, and maleate. Preferred salts include, but are not limited to, citrate and mesylate salts. The salts may also be solvates, including ethanol solvates, and hydrates.

Salts of the delivery agent compounds of the present invention may be prepared by methods known in the art. For example, citrate salts and mesylate salts may be prepared in ethanol, toluene and citric acid.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O)—; —OOC—, —COO—, —NHC(O)O—, —OC(O)NH—, —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Non-limiting examples of delivery agent compounds of formula I include those shown below and pharmaceutically acceptable salts thereof:

Compound 1

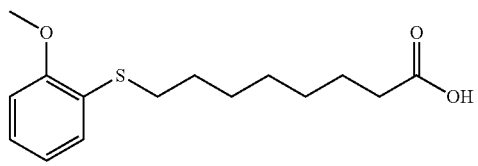

8-(2-Methoxy-phenylsulfanyl)-octanoic acid

Compound 2

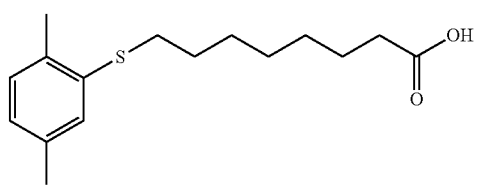

8-(2,5-Dimethyl-phenylsulfanyl)-octanoic acid

Compound 3

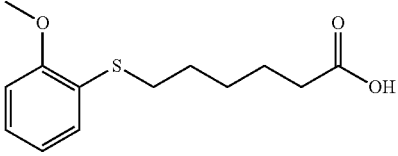

6-(2-Methoxy-phenylsulfanyl)-hexanoic acid

Compound 4

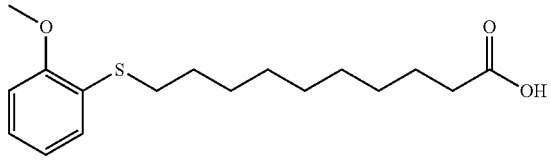

10-(2-Methoxy-phenylsulfanyl)-decanoic acid

Compound 5

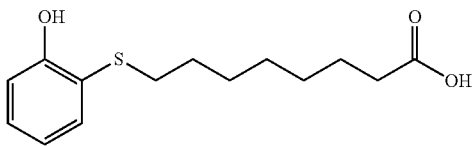

8-(2-Hydroxy-phenylsulfanyl)-octanic acid

Compound 6

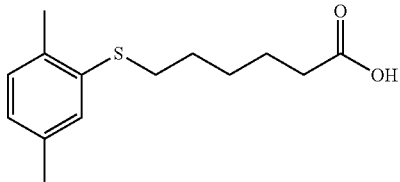

6-(2,5-Dimethyl-phenylsulfanyl)-hexanoic acid

Compound 7

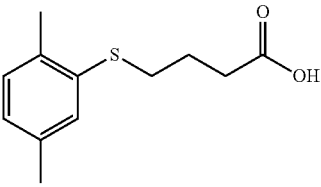

4-(2,5-Dimethyl-phenylsulfanyl)-butyric acid

Compound 8

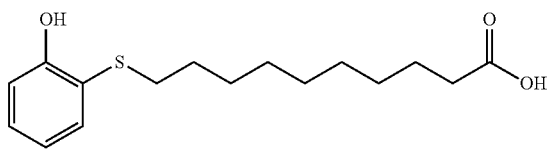

10-(2-Hydroxy-phenylsulfanyl)-decanoic acid

Compound 9

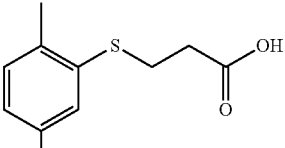

3-(2,5-Dimethyl-phenylsulfanyl)-propionic acid

Compound 10

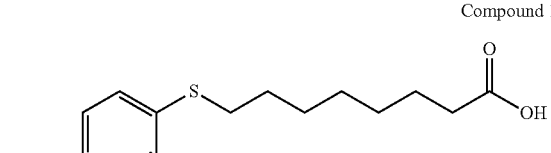

8-(4-Methoxy-phenylsulfanyl)-octanoic acid

Compound 11

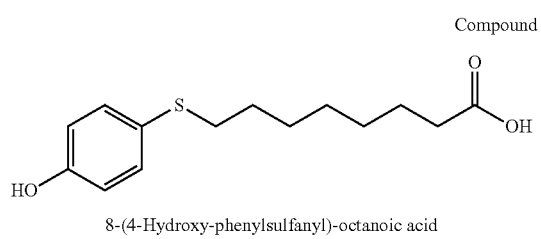

8-(4-Hydroxy-phenylsulfanyl)-octanoic acid

Compound 12

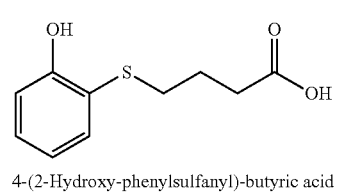

4-(2-Hydroxy-phenylsulfanyl)-butyric acid

Compound 13

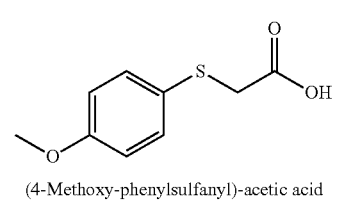

(4-Methoxy-phenylsulfanyl)-acetic acid

Compound 14

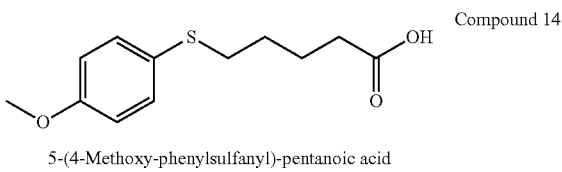

5-(4-Methoxy-phenylsulfanyl)-pentanoic acid

Compound 15

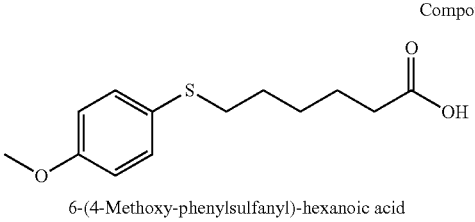

6-(4-Methoxy-phenylsulfanyl)-hexanoic acid

Compound 16

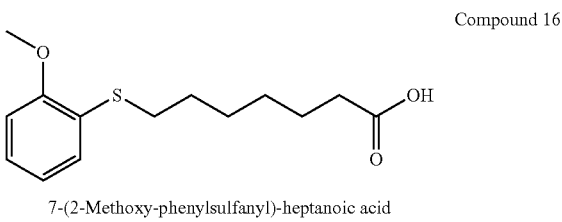

7-(2-Methoxy-phenylsulfanyl)-heptanoic acid

Compound 17

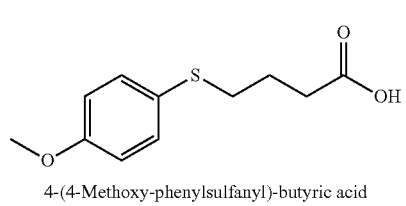

4-(4-Methoxy-phenylsulfanyl)-butyric acid

Compound 18

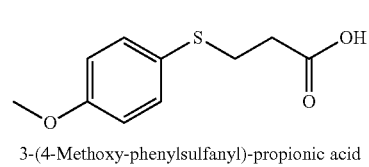

3-(4-Methoxy-phenylsulfanyl)-propionic acid

Compound 19

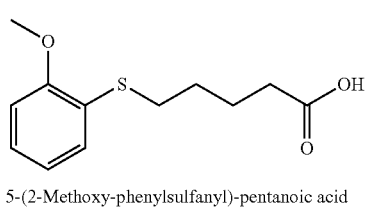

5-(2-Methoxy-phenylsulfanyl)-pentanoic acid

Compound 20

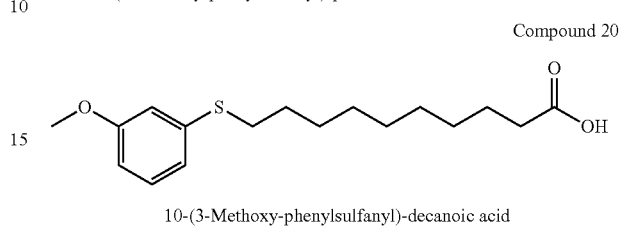

10-(3-Methoxy-phenylsulfanyl)-decanoic acid

Compound 21

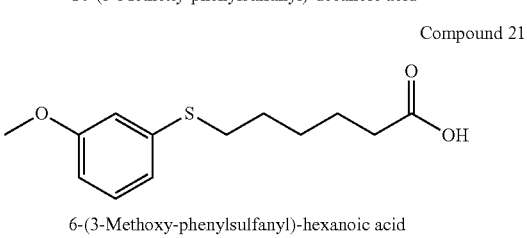

6-(3-Methoxy-phenylsulfanyl)-hexanoic acid

Compound 22

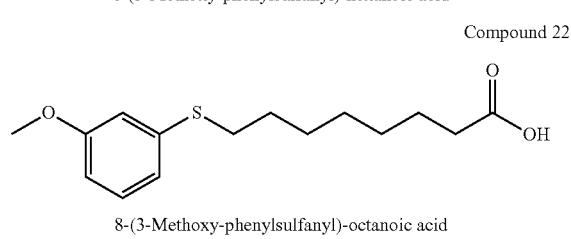

8-(3-Methoxy-phenylsulfanyl)-octanoic acid

Compound 23

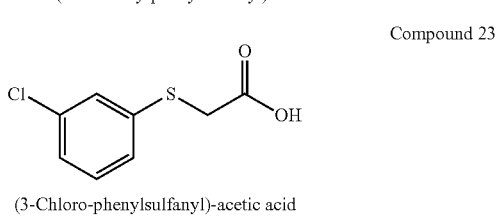

(3-Chloro-phenylsulfanyl)-acetic acid

Compound 24

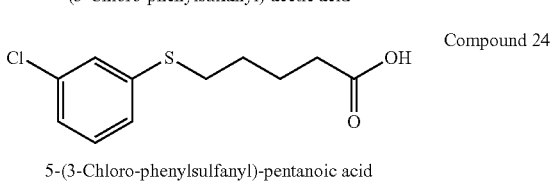

5-(3-Chloro-phenylsulfanyl)-pentanoic acid

Compound 25

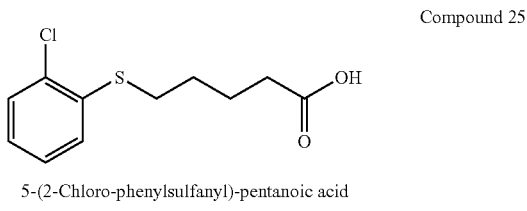

5-(2-Chloro-phenylsulfanyl)-pentanoic acid

Compound 26

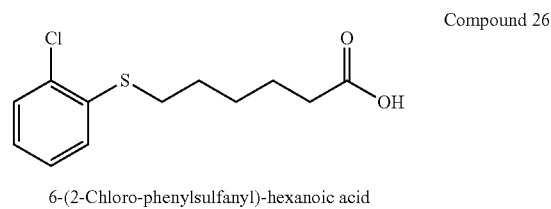

6-(2-Chloro-phenylsulfanyl)-hexanoic acid

Compound 27
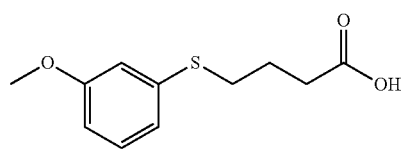
4-(3-Methoxy-phenylsulfanyl)-butyric acid

Compound 28
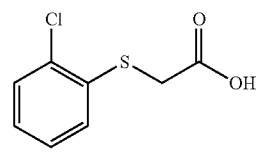
(2-Chloro-phenylsulfanyl)-acetic acid

Compound 29
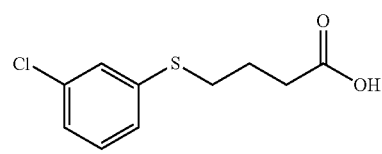
4-(3-Chloro-phenylsulfanyl)-butyric acid

Compound 30
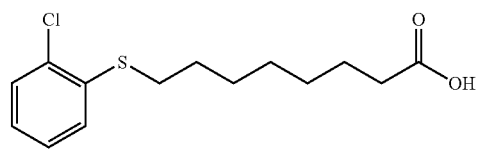
8-(2-Chloro-phenylsulfanyl)-octanoic acid

Compound 31
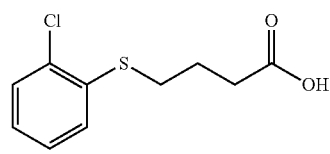
4-(2-Chloro-phenylsulfanyl)-butyric acid

Compound 32
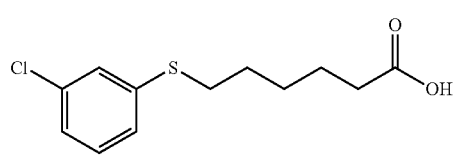
6-(3-Chloro-phenylsulfanyl)-hexanoic acid

Compound 33
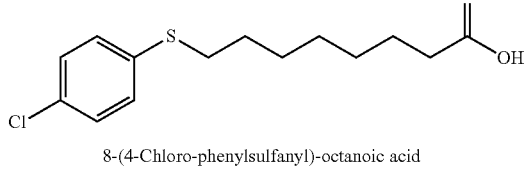
8-(4-Chloro-phenylsulfanyl)-octanoic acid

Compound 34
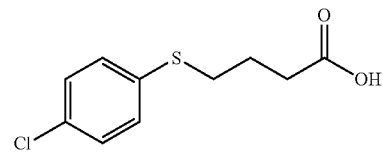
4-(4-Chloro-phenylsulfanyl)-butyric acid

Compound 35
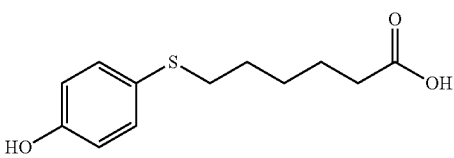
6-(4-Hydroxy-phenylsulfanyl)-hexanoic acid

Compound 36
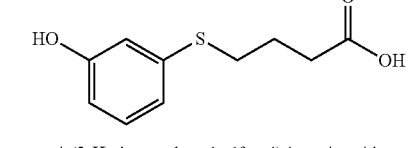
4-(3-Hydroxy-phenylsulfanyl)-butyric acid

Compound 37
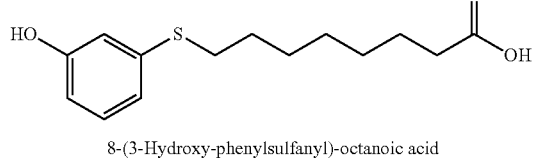
8-(3-Hydroxy-phenylsulfanyl)-octanoic acid

Compound 38
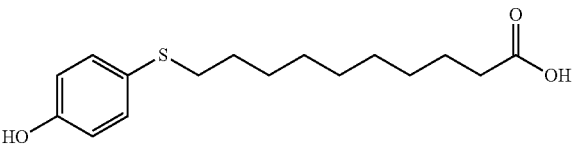
10-(4-Hydroxy-phenylsulfanyl)-decanoic acid

Compound 39
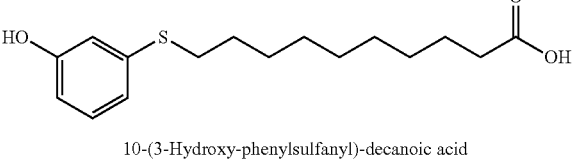
10-(3-Hydroxy-phenylsulfanyl)-decanoic acid

Compound 40
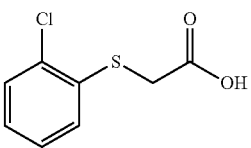
(2,5-Dichloro-phenylsulfanyl)-acetic acid

Compound 41
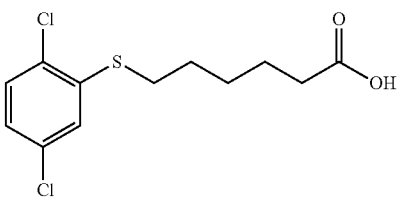
6-(2,5-Dichloro-phenylsulfanyl)-hexanoic acid

Compound 42
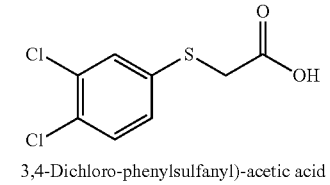
(3,4-Dichloro-phenylsulfanyl)-acetic acid

Compound 43
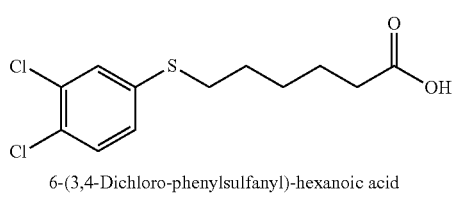
6-(3,4-Dichloro-phenylsulfanyl)-hexanoic acid

Compound 44
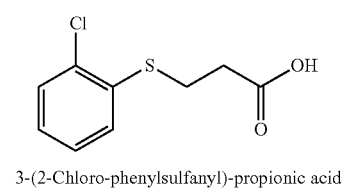
3-(2-Chloro-phenylsulfanyl)-propionic acid

Compound 45
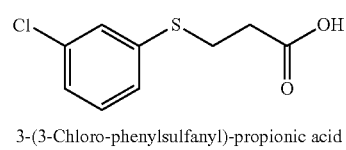
3-(3-Chloro-phenylsulfanyl)-propionic acid

Compound 46
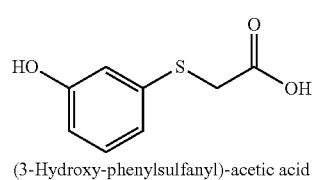
(3-Hydroxy-phenylsulfanyl)-acetic acid

Compound 47
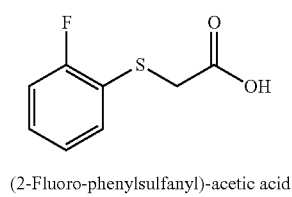
(2-Fluoro-phenylsulfanyl)-acetic acid

Compound 48
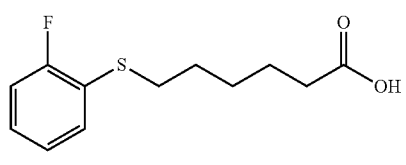
6-(2-Fluoro-phenylsulfanyl)-hexanoic acid

Compound 49
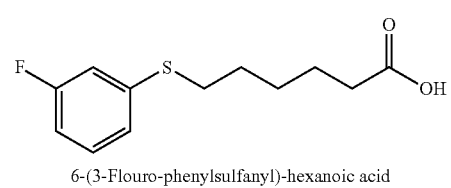
6-(3-Flouro-phenylsulfanyl)-hexanoic acid

Compound 50
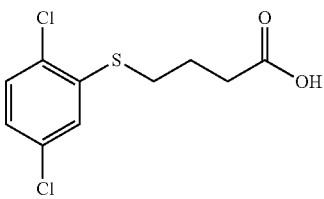
4-(2,5-Dichloro-phenylsulfanyl)-butyric acid

Compound 51
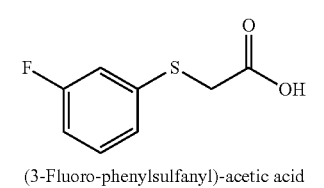
(3-Fluoro-phenylsulfanyl)-acetic acid

Compound 52
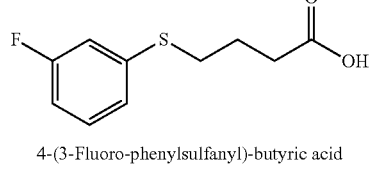
4-(3-Fluoro-phenylsulfanyl)-butyric acid

Compound 53
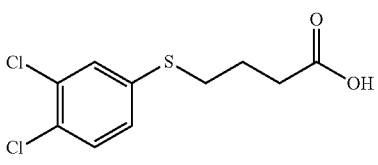
4-(3,4-Dichloro-phenylsulfanyl)-butyric acid

Compound 54
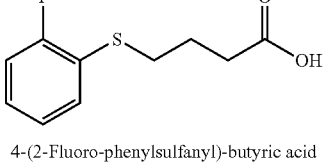
4-(2-Fluoro-phenylsulfanyl)-butyric acid

Compound 55
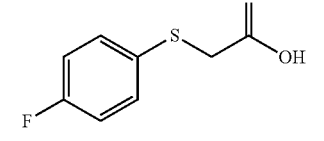
(4-Fluoro-phenylsulfanyl)-acetic acid

Compound 56
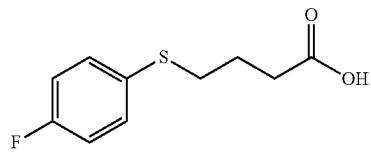
4-(4-Fluoro-phenylsulfanyl)-butyric acid

Compound 57
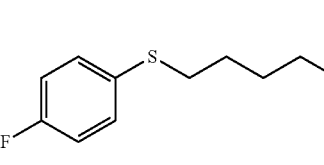
6-(4-Flouro-phenylsulfanyl)-hexanoic acid

Compound 58

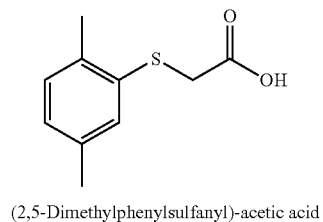

(2,5-Dimethylphenylsulfanyl)-acetic acid

Compound 59

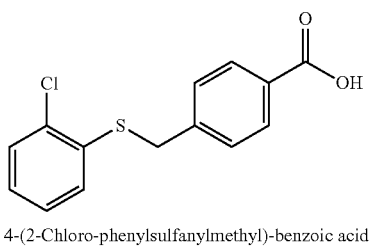

4-(2-Chloro-phenylsulfanylmethyl)-benzoic acid

Compound 60

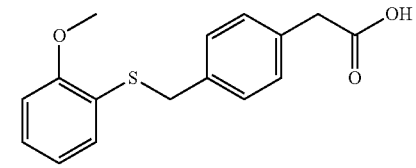

[4-(2-Methoxy-phenylsulfanylmethyl)-phenyl]-acetic acid

Compound 61

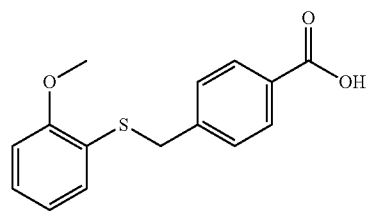

4-(2-Methoxy-phenylsulfanylmethyl)-benzoic acid

Compound 62

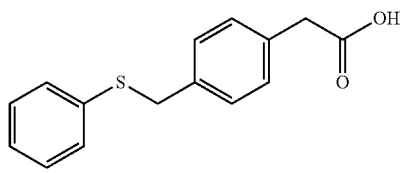

(4-Phenylsulfanylmethyl-phenyl)-acetic acid

Compound 63

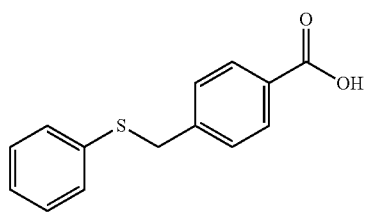

4-Phenylsulfanylmethyl-benzoic acid

Compound 64

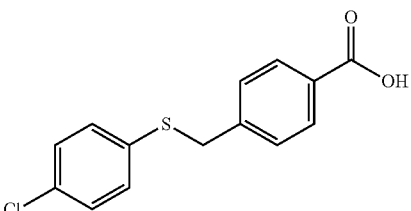

4-(4-Chloro-phenylsulfanylmethyl)-benzoic acid

Compound 65

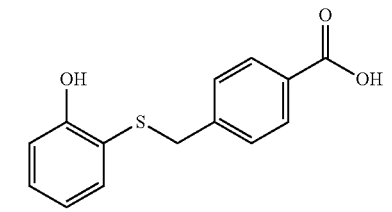

4-(2-Hydroxy-phenylsulfanylmethyl)-benzoic acid

Compound 66

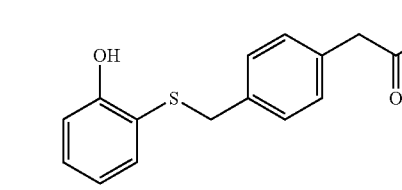

[4-(2-Hydroxy-phenylsulfanylmethyl)-phenyl]-acetic acid

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α-interferon (e.g., interferon alfacon-1 (available as Infergen® from InterMune, Inc. of Brisbane, Calif.)), β-interferon and γ-interferon; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as sumatriptan, almotriptan, naratriptan, rizatriptan, frovatriptan, eletriptan, BIBN-4096BS and other calcitonin gene-related proteins antagonists; glucagon-like peptide 1 (GLP-1); Argatroban; glucagon; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The pharmaceutical composition of the present invention comprises one or more delivery agent compounds of the present invention, and one or more active agents (e.g., biologically active agents). In one embodiment, one or more of the delivery agent compounds, or salts of these compounds, may be used as a delivery agent by mixing delivery agent compounds with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process. Alternatively, the delivery agent compound and active agent can be separately administered in sequential fashion.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitors.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

Generally, the amount of delivery agent compound in the composition is an amount effective to facilitate delivery of the active agent. The total amount of active agent and delivery agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects. Generally, the weight ratio of delivery agent to active agent ranges from about 1000:1 or 800:1 to about 10:1 or 1:10, and preferably ranges from about 400:1 or 200:1 to about 100:1 or 25:1. Other ranges are contemplated to be within acceptable ranges for delivery of some active compounds, such as from about 100:1 or 50:1 to about 5:1 or 2.5:1, or from about 60:1 or 30:1 to about 1:1 or 0.5:1. Such ranges and ratios can be determined by one skilled in the art.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the compounds and active agents have utility in the delivery of active agents to selected biological systems and in an increased or improved bio-availability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as any one of the diseases or conditions listed in the table below, in an animal by administering the composition of the present invention.

Preferably, an effective amount of the composition for the treatment or prevention of the desired disease or for achieving the desired physiological effect is administered. Specific indications for active agents can be found in the *The Physicians' Desk Reference* (58$^{th}$ Ed., 2004, Medical Economics Company, Inc., Montvale, N.J.), and Fauci, A S, et. al., *Harrison's Principles of Internal Medicine* (14$^{th}$ Ed., 1998, McGraw-Hill Health Professions Division, New York. Both of these references are herein incorporated by reference in their entirety. The active agents in the table below include their analogs, fragments, mimetics, and polyethylene glycol-modified derivatives (e.g., the PEGylated derivative of granulocyte colony stimulating factor sold as Neulasta®).

| Active Agent | Disease and Physiological Effect |
| --- | --- |
| Growth hormones (including human recombinant growth hormone and growth-hormone releasing factors and its analogs) | Growth disorders |
| Interferons, including α, β and γ | Viral infection, including chronic cancer, hepatitis, and multiple sclerosis |
| Interleukins (e.g. Interleukin-1; interleukin-2) | Viral infection; cancer; cell mediated immunity; and transplant rejection; |
| Insulin; Insulin-like growth factor IGF-1 | Diabetes |
| Immune Globulins, such as IVIg | smallpox, rabies, and diphtheria, Alzheimer's Disease; Primary immunodeficiencies; Acute Guillain-Barré syndrome; Chronic idiopathic demyelinating polyneuropathy (CIDP); Myasthenia gravis, polymyositis, and dermatomyositis; neonatal immune thrombocytopenia, heparin-induced thrombocytopenia, and antiphospholipid antibody syndrome: Posttransfusion purpura. |
| Heparin | Treatment and Prevention of Thrombosis, including (Deep Vein Thrombosis); prevention of blood coagulation |
| Calcitonin | Osteoporosis; diseases of the bone; bone pain; analgesic (including pain associated with osteoporosis or cancer) |
| Erythropoietin, Pegylated erythropoietin. | Anemia; HIV/HIV-therapy Associated Anemia; Chemotherapeutically-Induced Anemia |
| Atrial naturetic factor | Vasodilation |
| Antigens | Infection |
| CPHPC | Reduction of amyloid deposits and systemic amyloidoisis often (but not always) in connection with Alzheimer's disease, Type II diabetes, and other amyloid-based diseases |
| Monoclonal antibodies | To prevent graft rejection; cancer; used in assays to detect diseases |
| Somatostatin/octreotide | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy |
| Protease inhibitors | HIV Infection/AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; Leutinizing Hormone; follicle stimulating hormone | Regulate reproductive function |
| Glucocerebrosidase | Gaucher disease (to metabolize lipoprotein) |
| Thrombopoietin | Thrombocytopenia |
| Filgrastim (Granulocyte Colony Stimulating Factor); GM-CSF, (sargramostim) and their Pegylated forms | shorten the duration of chemotherapy-induced neutropenia and thus treat or prevent infection in chemotherapy patients; Inhibit the growth of or to kill Mycobacterium Intracellular Avium Infection (MAC) |
| RNAi | Huntington, Alzheimers, Viral Infections (HIV, Hepatitis A, B or C, RSV), Cancers; Macular Degeneration |
| Prostaglandins | Hypertension |
| Cyclosporin | Transplant rejection; psoriasis, inflammatory alopecias; Sjogren's syndrome; Keratoconjunctivitis Sicca |
| Vasopressin | Nocturnal Enuresis; antidiuretic |
| Cromolyn sodium; | Asthma; allergies |

-continued

| Active Agent | Disease and Physiological Effect |
|---|---|
| Vancomycin | Treat or prevent antimicrobial-induced infections including, but not limited to methacillin-resistant *Staphalococcus aureus* and *Staph. epidermiditis* |
| gallium salts (such as gallium nitrate) | Osteoporosis; Paget's disease; Inhibits osteoclasts; Promotes osteoblastic activity, hypercalcemia, including cancer related hypercalcemia, urethral (urinary tract) malignancies; anti-tumors, cancers, including urethral and bladder cancers; lymphoma; malignancies (including bladder cancer); leukemia; management of bone metastases (and associated pain); muliple myeloma, attenuate immune response, including allogenic transplant rejections; disrupt iron metabolism; promote cell migration; wound repair; to attenuate or treat infectious processes of *mycobacterium* species, including but not limited to *mycobacterium tubercolosis*, and *mycobacterium avium* complex |
| Desferrioxamine (DFO) | Iron overload |
| Parathyroid hormone (PTH), including its fragments. | Osteoporosis; Diseases of the bone |
| Antimicrobials | Infection including but not limited to gram-positive bacterial infection |
| Vitamins | Treat and prevent Vitamin deficiencies |
| Bisphosphonates | Osteoporosis; Paget's disease; bone tumors and metastases (and associated pain); Breast cancer; including as adjuvant therapy for early stage breast cancer; management of bone metastases (and associated pain), including bone metastases associate with breast cancer, prostate cancer, and lung cancer; Inhibits osteoclasts; Promotes osteoblastic activity; treat and/or prevent bone mineral density (bmd) loss; multiple myeloma; prevention of bone complications related to malignant osteolysis; fibrous dysplasia; pediatric osteogenesis imperfecta; hypercalcemia, urethral (urinary tract) malignancies; reflex sympathetic dystropy synodrome, acute back pain after vertebral crush fracture, chronic inflammatory joint disease, renal bone disease, extrosseous calcifications, analgesic, vitamin D intoxication, periarticular ossifications |
| BIBN4096BS - (1-Piperidinecarboxamide•N-[2-[[5-amino-1-[[4-(4-pyridinyl)-1-piperazinyl]carbonyl]pentyl]amino]-1-[(3,5-dibromo-4-hydroxyphenyl)methyl]-2-oxoethyl]-4(1,4-dihydro-2-oxo-3(2H0-quinazolinyl)-•[R-(R*,S*)]-) | Anti-migraine; calcitonin gene- related peptide antagonist |
| Glucagon | improving glycemic control (e.g. treating hypoglycemia and controlling hypoglycemic reactions), obesity; a diagnostic aid in the radiogical examination of the stomach, duodenum, small bowel and colon; Treat acute poisoning With Cardiovascular Agents including, but not limited to, calcium channel blockers, beta blockers |
| GLP-1, Exendin - 3, Exendin - 4, Obestatin | Diabetes; improving glycemic control (e.g. treating hypoglycemia and controlling hypoglycemic reactions), obesity |
| dipeptidyl peptidase IV (DPP-4) inhibitors | Diabetes; improving glycemic control (e.g. treating hypoglycemia), obesity |
| acyclovir | Used to treat herpes infections of the skin, lip and genitals; herpes zoster (shingles); and chickenpox |
| HIV Entry Inhibitors (e.g. Fuzeon) | Inhibit entry of HIV into host cells |
| Sumatriptin, almotriptan, naratriptan, rizatriptan, frovatriptan and eletriptan (piperidinyloxy)phenyl, (piperidinyloxy)pyridinyl, (piperidinylsulfanyl)phenyl and (piperidinylsulfanyl)pyridinyl compounds | anti-migraine serotonin agonists |
| Neuraminidase inhibitors: peramivir, zanamivir, oseltamivir, BCX-1898, BCX-1827, BCX-1989, BCX 1923, BCX 1827 and A315675; M2 inhibitors: amantadine, rimantadine; Nucleoside/Nucleotide Reverse Transcriptase Inhibitors, Non-nucleoside Reverse Transcriptase Inhibitors, Protease Inhibitors, Fusion inhibitors: thiovir, thiophosphonoformate, foscarnet, enfuviritide, zidovudine, didanosine, zalcitabine, | Antivirals |

-continued

| Active Agent | Disease and Physiological Effect |
|---|---|
| stavudine, lamivudine, emtricitabine, abacavir, azidothymidine, tenofovir disoproxil, delavridine, efavirenz, nevirapine, ritonavir, nelfinavir mesylate, saquinvir mesylate, indinavir sulfate, amprenavir, lopinavir, lopinavir, fosamprenavir calcium, atazanavir sulfate | |
| Peptide YY (PYY) and PYY-like Peptides (e.g. PYY[3-36]) | Obesity, Diabetes, Eating Disorders, Insulin-Resistance Syndromes |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternatively, the circulating levels of the active agent itself can be measured directly.

One embodiment of the present invention provides a pharmaceutical composition comprising an effective amount of insulin and an effective amount of at least one of the delivery agents described herein. For example, one embodiment of the present invention provides a pharmaceutical composition comprising about 50 to 800 mg/kg (e.g. 200 mg/kg) of insulin and about 0.1 to 2.0 mg/kg (e.g. 0.5 mg/kg) of any one of the delivery agent compounds of the present invention.

Yet another embodiment is method of treating diseases characterized by hyperglycemia, such as diabetes, comprising administering a pharmaceutical composition of the present invention to a subject.

One embodiment of the present invention provides a pharmaceutical composition comprising an effective amount of heparin and an effective amount of at least one of the delivery agents described herein. For example, one embodiment of the present invention provides a pharmaceutical composition comprising about 5 to 125 mg/kg (e.g. 25 mg/kg or 80 mg/kg) of heparin and about 5 to 500 mg/kg (e.g. 50 mg/kg or 200 mg/kg) of any one of the delivery agent compounds of the present invention.

Yet another embodiment is method of treating or preventing disease characterized by intravascular thrombi by administering an effective amount of heparin and an effective amount of a delivery agent of the present invention to a subject.

Yet another embodiment is method of preventing DVT in susceptible individuals by administering an effective amount of heparin and an effective amount of a delivery agent compound of the present invention to a subject.

One embodiment of the present invention provides a pharmaceutical composition comprising an effective amount of rhGH and an effective amount of at least one of the delivery agents described herein. For example, one embodiment of the present invention provides a pharmaceutical composition comprising about 0.25 to 10 mg/kg (e.g. 3 mg/kg) of rhGH and about 50 to 500 mg/kg (e.g. 200 mg/kg) of any one of the delivery agent compounds of the present invention.

Yet another embodiment is method of treating or preventing short stature by administering an effective amount of rhGH and an effective amount of at least one delivery agent compound of the present invention to a subject.

Yet another embodiment is method of treating or preventing a disease which requires supplementation of growth hormone by administering an effective amount of at least one delivery agent compound of the present invention to a subject.

One embodiment of the present invention provides a pharmaceutical composition comprising an effective amount of LHRH and an effective amount of at least one of the delivery agents described herein. For example, one embodiment of the present invention provides a pharmaceutical composition comprising about 0.1 to 10 mg/kg (e.g. 1 mg/kg) of LHRH and about 50-500 mg/kg (e.g. 200 mg/kg) of any one of the delivery agent compounds of the present invention.

Yet another embodiment is method of treating or preventing infertility in men or women which requires supplementation of LHRH by administering an effective amount of LHRH and an effective amount of at least one delivery agent of the present invention to a subject.

Yet another embodiment is method of treating or preventing a disease which requires supplementation of LHRH by administering an effective amount of LHRH and an effective amount of at least one delivery agent of the present invention to a subject.

One embodiment of the present invention provides a pharmaceutical composition comprising an effective amount of caspofungin acetate (e.g. Cancidas®) and an effective amount of at least one of the delivery agents described herein. For example, one embodiment of the present invention provides a pharmaceutical composition comprising about 5 to 125 mg/kg (e.g. 25 mg/kg) of caspofungin acetate and about 50 to 500 mg/kg (e.g. 200 mg/kg) of any one of the delivery agent compounds of the present invention.

Yet another embodiment is method of treating or preventing candidiasis or other systemic or localized fungal infections by administering an effective amount of caspofungin acetate and an effective amount of a delivery agent of the present invention to the subject.

EXAMPLES

The following examples illustrate the present invention without limitation.

Example 1—Preparation of
8-(2-Methoxy-phenylsulfanyl)-octanoic acid
(Compound 1)

To a 250 mL flask, equipped with a magnetic stir bar, was added ethyl 8-bromo-octanoate (13.8 mL, 66 mmol), 2-methoxybenzenethiol (8.0 mL, 66 mmol), and 80 mL ethyl alcohol. The reaction vessel was cooled with an external ice bath while potassium hydroxide (5.2 g 93 mmol) was added. The reaction was allowed to warm to room temperature and stirred 16 hours under a nitrogen atmosphere. The white precipitate was removed by suction filtration and solvent removed under reduced pressure. The concentrate was then dissolved in 10 mL ethyl alcohol, treated with 90 mL of aqueous 1 N sodium hydroxide solution and heated for 1 hour at reflux. The solution was acidified to pH 1 with aqueous 1 N hydrochloric acid and cooled to 4° C. The product (16.2 g, 87%) was isolated by filtration as an off-white powder, mp 62-63° C. Found: C: 63.79%, H: 7.91% S: 11.25%; $C_{15}H_{22}O_3S$ requires C: 63.80%, H: 7.85%, S: 11.35%; 1H NMR (d6-DMSO): δ 7.21, d, 1H (aryl H); δ 7.15 td, 1H (aryl H); δ 6.96, d, 1H (aryl H); δ 6.92 td, 1H (aryl H); δ 3.8, s, 3H (OCH$_3$); δ 2.85, t, 2H (CH$_2$ α to S); δ 2.2, t, 2H (CH$_2$ α to COOH); δ 1.6-1.2, multiplet, 10H (rest of CH$_2$'s).

Example 2—Preparation of
8-(2,5-Dimethyl-phenylsulfanyl)-octanoic acid
(Compound 2)

To a 500 mL flask, equipped with a magnetic stir bar, was added ethyl 8-bromo-octanoate (10.8 mL, 52 mmol), 2,5-dimethylbenzenethiol (7.0 mL, 52 mmol), and 72 mL ethyl alcohol. The reaction vessel was cooled with an external ice bath while potassium hydroxide (4.45 g, 79 mmol) was added. The reaction was allowed to warm to room temperature and stirred 16 hours under a nitrogen atmosphere. A second amount of potassium hydroxide (2.0 g, 36 mmol) was added with 130 mL of ethyl alcohol. The reaction was allowed to stir at room temperature for 18 hours. To the reaction mixture was added 50 mL of aqueous 1 N sodium hydroxide solution and was heated for 1 hour at reflux. The solution was acidified to pH 1 with aqueous 1 N hydrochloric acid and cooled to 4° C. The product (13.9 g, 96%) was isolated by filtration as an off-white powder, mp 60-63° C. Found: C: 68.69%, H: 8.82% S: 11.26%; $C_{16}H_{24}O_2S$ requires C: 68.53%, H: 8.63%, S: 11.43%; 1H NMR (d6-DMSO): δ 12.0, broad s, 1H (COOH); δ 7.07, s, 1H (aryl H); δ 7.06, d, 1H (aryl H); δ 6.88, d, 1H (aryl H); δ 2.90, t, 2H (CH$_2$ α to S); δ 2.25, s, 3H (aryl-CH$_3$); δ 2.21, s, 3H (Aryl-CH$_3$); δ 2.19, t, 2H (CH$_2$ α to COOH); δ 1.6-1.2, multiplet, 10H (rest of CH$_2$'s).

Example 3—Preparation of
6-(2-Methoxy-phenylsulfanyl)-hexanoic acid
(Compound 3)

To a 500 mL flask, equipped with a magnetic stir bar, was added ethyl 6-bromohexanoate (12.0 mL, 67 mmol), 2-methoxybenzenethiol (8.2 mL, 67 mmol), and 52 mL ethyl alcohol. The reaction vessel was cooled with an external ice bath while potassium hydroxide (7.72 g, 138 mmol) was added. The reaction was allowed to stir at room temperature for 18 hours under nitrogen atmosphere. Water (100 mL) and 50 mL of aqueous 1 N sodium hydroxide solution were added and the mixture allowed to stir at room temperature for 18 hours. Ethyl alcohol was distilled at atmospheric pressure. The resulting solution was acidified to pH 1 with aqueous 1 N hydrochloric acid and cooled to 4° C. for 18 hours. The product (16.3 g, 95%) was isolated by filtration as an off-white powder, mp 81-82° C. Found: C: 60.70%, H: 7.08% S: 12.46%; $C_{13}H_{18}O_3S$ requires C: 60.87%, H: 7.17%, S: 12.50%; 1H NMR (d6-DMSO): δ 12.0, broad s, 1H (COOH); δ 7.20, dd, 1H (aryl H); δ 7.16, dt, 1H (aryl H); δ 6.96, dd, 1H (aryl H); δ 6.93, dt, 1H (aryl H); δ 3.80, s, 3H (OCH$_3$); δ 2.86, t, 2H (CH$_2$ α to S); δ 2.20, t, 2H (CH$_2$ α to COOH); δ 1.6-1.3, multiplet, 6H (rest of CH$_2$'s).

Example 4—Preparation of
10-(2-Methoxy-phenylsulfanyl)-decanoic acid
(Compound 4)

Prepared analogously to Compound 3 with ethyl 10-bromo-decanoate (11.47 g, 41.1 mmol), 2-methoxybenzenethiol (5.0 mL, 41.1 mmol), 40 mL ethyl alcohol, and potassium hydroxide (7.00 g, 124.8 mmol). The product (12.3 g, 96%) was isolated by filtration as an off-white powder, mp 65-66° C. Found: C: 65.71%, H: 8.38% S: 10.25%; $C_{17}H_{26}O_3S$ requires C: 65.77%, H: 8.44%, S: 10.33%; 1H NMR (d6-DMSO): δ 12.0, broad s, 1H (COOH); δ 7.20, dd, 1H (aryl H); δ 7.16, dt, 1H (aryl H); δ 6.96, dd, 1H (aryl H); δ 6.93, dt, 1H (aryl H); δ 3.80, s, 3H (OCH$_3$); δ 2.85, t, 2H (CH$_2$ α to S); δ 2.18, t, 2H (CH$_2$ α to COOH); δ 1.6-1.2, multiplet, 14H (rest of CH$_2$'s).

Example 5—Preparation of
8-(2-Hydroxy-phenylsulfanyl)-octanoic acid
(Compound 5)

To a 150 mL round bottom flask equipped with a reflux condenser and magnetic stir bar was added 8-(2-methoxy-phenylsulfanyl)-octanoic acid (4.32 g, 15.3 mmol) and 25 mL methylene chloride. The mixture was cooled with an external ice bath. Boron tribromide solution (25 ml of a 1 M solution in methylene chloride, 25 mmol) was added and the external ice bath removed. After 10 minutes the reaction was heated to reflux for 10 minutes and allowed to cool to room temperature. Boron tribromide solution (25 ml of a 1 M solution in methylene chloride, 25 mmol) was added and the reaction allowed to mix at room temperature for 15 minutes. The reaction was cooled with an external ice bath and then quenched with 75 mL of water. This mixture was allowed to stir at room temperature for 18 hours. The layers were separated and the aqueous layer was extracted with methylene chloride (2×40 mL). The organic layers were combined and washed with water (40 mL) and then brine solution (40 mL). The organic layer was dried over sodium sulfate, filtered, and then the solvent removed under reduced pressure. The residue was dissolved in aqueous 1 N sodium hydroxide (25 mL) and diluted with 100 mL water. The solution was acidified to pH 1 with aqueous 1 N hydrochloric acid and cooled to 4° C. for 14 days. The brown solid was collected by suction filtration. Solid was dissolved in aqueous 1 N sodium hydroxide solution (25 mL) and diluted with 75 mL water. The solution was acidified to pH 8 with aqueous 1 N hydrochloric acid and cooled to 4° C. The pH was the lowered slowly by the addition of 2-3 drops of aqueous 1 N hydrochloric acid two times a day for 21 days at 4° C. At end of time period 5 mL of aqueous 1 N hydrochloric acid was added to ensure pH 1 and solution allowed to set for 18 hours at 4° C. The off-white product and one solid brown chunk were collected by suction filtration and the brown chunk removed with forceps. The product (2.54 g, 62%) was isolated as an off-white solid, mp 49-50° C. Found: C: 62.52%, H: 7.35% S: 101.91%; $C_{14}H_{20}O_3S$ requires C: 62.47%, H: 7.52%, S: 11.91%; 1H NMR (d6-DMSO): δ 12.0, broad s, 1H (COOH); δ 9.70, s, 1H (Ar—OH); δ 7.16, dd, 1H (aryl H); δ 7.01, dt, 1H (aryl H); δ 6.80, dd, 1H (aryl H); δ 6.77, dt, 1H (aryl H); δ 2.82, t, 2H (CH$_2$ α to S); δ 2.18, t, 2H(CH$_2$ α to COOH); δ 1.6-1.2, multiplet, 10H (rest of CH$_2$'s).

Example 6—Preparation of 6-(2,5-Dimethyl-phenylsulfanyl)-hexanoic acid (Compound 6)

To a 500 mL flask, equipped with a magnetic stir bar, was added ethyl 6-bromohexanoate (5.25 mL, 30 mmol), 2,5-dimethylbenzenethiol (4.0 mL, 30 mmol), and 100 mL ethyl alcohol. The reaction vessel was cooled with an external ice bath while potassium hydroxide (5.32 g, 95 mmol) was added. The external ice bath was removed and the reaction was allowed to stir at room temperature for 18 hours under a nitrogen atmosphere. Water (100 mL) was added and the reaction was allowed to mix at room temperature for an additional 18 hours. Ethyl alcohol was removed under reduced pressure. The remaining solution was acidified to pH 1 with aqueous 1 N hydrochloric acid and cooled to 4° C. for 18 hours. The product (6.39 g, 86%) was isolated by filtration as a white solid, mp 61-62° C. Found: C: 66.80%, H: 8.00% S: 12.68%; $C_{14}H_{20}O_2S$ requires C: 66.63%, H: 7.99%, S: 12.71%; 1H NMR (d6-DMSO): (COOH, not visible due to water in sample); δ 7.08, s, 1H (aryl H); δ 7.06, d, 1H (aryl H); δ 6.88, d, 1H (aryl H); δ 2.90, t, 2H($CH_2$ α to S); δ 2.26, s, 3H (aryl-$CH_3$); δ 2.21, s, 3H (Aryl-$CH_3$); δ 2.19, t, 2H ($CH_2$ α to COOH); δ 1.65-1.35, multiplet, 6H (rest of $CH_2$'s).

Example 7—Preparation 4-(2,5-Dimethyl-phenylsulfanyl)-butyric acid (Compound 7)

Prepared analogously to Compound 6 with ethyl 4-bromobutyrate (2.88 mL, 15 mmol), 2,5-dimethylbenzenethiol (2.0 mL, 15 mmol), potassium hydroxide (2.54 g, 45 mmol), and 100 mL ethyl alcohol. The product (2.87 g, 87%) isolated as an off-white solid, mp 61-62° C. Found: C: 64.18%; H: 7.26% S: 14.39%; $C_{12}H_{16}O_2S$ requires C: 64.06%, H: 7.20%, S: 14.25%; 1H NMR (d6-DMSO): δ 12.14, s, 1H (COOH); δ 7.13, s, 1H (aryl H); δ 7.08, d, 1H (aryl H); δ 7.06, d, 1H (aryl H); δ 2.94, t, 2H ($CH_2$ α to S); δ 2.38, t, 2H ($CH_2$ α to COOH); δ 2.26, s, 3H (aryl-$CH_3$); δ 2.22, s, 3H (Aryl-$CH_3$); δ 1.78, quintuplet, 2H (other $CH_2$'s).

Example 8—Preparation of 10-(2-Hydroxy-phenylsulfanyl)-decanoic acid (Compound 8)

Prepared analogously to Compound 3 with 2-hydroxybenzenethiol (1.5 mL, 15 mmol), ethyl 10-bromodecanoate (4.16 g, 15 mmol), potassium hydroxide (2.49 g, 44 mmol), 10 mL ethyl alcohol, aqueous 1 N sodium hydroxide solution (4 mL), and water (15 mL). Product was further purified by recrystallization from hexanes twice. The product (1.81 g, 41%) was isolated as an off-white solid, mp 58-59° C. Found: C: 64.27%, H: 8.07% S: 10.61%; $C_{16}H_{24}O_3S$ requires C: 64.32%, H: 8.19%, S: 10.73%; 1H NMR (d6-DMSO): δ 12.00, broad s, 1H (COOH); δ 9.70, broad s, 1H (Aryl-OH); δ 7.16, d, 1H (aryl H); δ 7.00, t, 1H (aryl H); δ 6.77, multiplet, 2H (other aryl H's); δ 2.82, t, 2H ($CH_2$ α to S); δ 2.18, t, 2H ($CH_2$ α to COOH); δ 1.60-1.15, multiplet, 14H (rest of $CH_2$'s).

Example 9—Preparation of 3-(2,5-Dimethyl-phenylsulfanyl)-propionic acid (Compound 9)

Prepared analogously to Compound 6 with 2,5-dimethyl-benzenethiol (3.0 mL, 22 mmol), ethyl 3-bromopropionate (4.04 g, 22 mmol), potassium hydroxide (3.49 g, 62 mmol), 100 mL ethyl alcohol and water (20 mL). The product (2.57 g, 55%) was isolated as a white solid, mp 100-102° C. Found: C: 62.83%, H: 6.76% S: 15.29%; $C_{11}H_{14}O_2S$ requires C: 62.71%, H: 6.72%, S: 15.22%; 1H NMR (d6-DMSO): δ 12.40, broad s, 1H (COOH); δ 7.12, s, 1H (aryl H); δ 7.08, d, 1H (aryl H); δ 6.92, d, 1H (aryl H); δ 3.09, t, 2H ($CH_2$ α to S); δ 2.53, t, 2H ($CH_2$ α to COOH); δ 2.27, s, 3H (aryl-$CH_3$); δ 2.22, s, 3H (Aryl-$CH_3$).

Example 10—Preparation of 8-(4-Methoxy-phenylsulfanyl)-octanoic acid (Compound 10)

Prepared analogously to Compound 6 with 4-methoxybenzenethiol (4.0 mL, 33 mmol), ethyl 8-bromooctanoate (8.21 g, 33 mmol), potassium hydroxide (5.57 g, 99 mmol), 100 mL ethyl alcohol and water (65 mL). The product (8.76 g, 95%) was isolated as an off-white solid, mp 66-68° C. Found: C: 63.29%, H: 7.72% S: 11.27%; $C_{15}H_{22}O_3S$ requires C: 63.64%, H: 7.86%, S: 11.33%; 1H NMR (d6-DMSO): δ 7.30, d, 2H (aryl H's); δ 6.90, d, 2H (aryl H's); δ 3.74, s, 3H ($OCH_3$); δ 2.83, t, 2H($CH_2$ α to S); δ 2.17, t, 2H ($CH_2$ α to COOH); δ 1.60-1.20, multiplet, 10H (rest of $CH_2$'s).

Example 11—Preparation of 8-(4-Hydroxy-phenylsulfanyl)-octanoic acid (Compound 11)

To a 500 mL flask, equipped with a magnetic stir bar and a 60-mL addition funnel, was added 4-hydroxybenzenethiol (5.22 g, 41 mmol), potassium carbonate (7.03 g, 51 mmol), and 100 mL ethyl alcohol. The reaction vessel was cooled with an external ice bath. The addition funnel was charged with ethyl 8-bromooctanoate (10.41 g, 41 mmol) and 55 mL ethyl alcohol. This was then added drop-wise to the reaction vessel over 1 hour. The reaction was allowed to warm to room temperature and stirred for 18 hours under a nitrogen atmosphere. Ethyl alcohol was removed under reduced pressure. The residue was dissolved in 10 mL ethyl alcohol and 80 mL of aqueous 1 N sodium hydroxide solution and allowed to stir at room temperature for 18 hours. Solution was acidified to pH 1 with aqueous 1 N hydrochloric acid and cooled to 4° C. for 18 hours. The product (10.20 g, 92%) was isolated by filtration as an off-white solid, mp 94-95° C. Found: C: 61.79%, H: 7.55% S: 11.50%; $C_{14}H_{20}O_3S$ requires C: 62.07%, H: 7.55%, S: 121.84%; 1H NMR (d6-DMSO): δ 12.00, s, 1H (COOH); δ 10.55, s, 1H (Aryl-OH); δ 7.20, d, 2H (aryl H's); δ 6.72, d, 2H (aryl H's); δ 2.77, t, 2H ($CH_2$ α to S); δ 2.18, t, 2H($CH_2$ α to COOH); δ 1.55-1.20, multiplet, 10H (rest of $CH_2$'s).

Example 12—Preparation of 4-(2-Hydroxy-phenylsulfanyl)-butyric acid (Compound 12)

To a 250 mL round bottom was added 2-hydroxybenzenthiol (1.5 mL, 15 mmol), ethyl 4-bromobutyrate (2.14 mL, 15 mmol) and 100 mL ethyl alcohol. The mixture was cooled with an external ice bath. Potassium hydroxide (0.85 g, 15 mmol) was added and the mixture was allowed to warm to room temperature and stirred for 18 hours. Aqueous 1 N sodium hydroxide solution (80 mL) was added and the reaction allowed to mix at room temperature for 18 hours. Ethyl alcohol was removed under reduced pressure and the residue was acidified with aqueous 1 N hydrochloric acid solution to pH 7 and cooled to 4° C. The pH was lowered slowly by the addition of aqueous 1 N hydrochloric acid solution (1-3 drops a day for 60 days.) During this period, the reddish oily that initially forms was removed via pipette upon the initial formation of a white precipitate. The product (1.98 g, 62%) was isolated by suction filtration as an off-white solid, mp 77-78° C. Found: C: 56.54%, H: 5.84% S: 14.98%; $C_{10}H_{12}O_3S$ requires C: 56.58%, H: 5.70%, S: 15.11%; 1H NMR (d6-DMSO): δ 12.1, broad s, 1H (COOH); δ 9.75, s, 1H (Ar—OH); δ 7.19, dd, 1H (aryl H); δ 7.02, dt, 1H (aryl H); δ 6.78, multiplet, 2H (aryl H's); δ 2.85, t, 2H ($CH_2$ α to S); δ 2.34, t, 2H ($CH_2$ α to COOH); δ 1.72, quintuplet, 2H (other $CH_2$).

Example 13—Preparation of (4-Methoxy-phenylsulfanyl)-acetic acid (Compound 13)

To a mini-block tube was added 4-methoxybenzenthiol (2.50 mL, 20 mmol), ethyl bromoacetate (2.28 mL, 20 mmol), potassium hydroxide (2.33 g, 42 mmol) and 30 mL ethyl alcohol. The mixture was stirred under nitrogen for 18 hours. 5 mL of water and 5 mL of aqueous 1 N sodium hydroxide solution were added. The reaction mixture was heated (84° C.) for 3 hours under atmospheric conditions to remove a majority of the ethyl alcohol. The mixture was cooled to room temperature and acidified with aqueous 1 N hydrochloric acid to pH 1 and allowed to stir at room temperature for 18 hours. The product (3.22 g, 80%) was isolated by filtration as an off-white solid. 1H NMR (d6-DMSO): δ 12.66, broad s, 1H (COOH); δ 7.33, multiplet, 2H (aryl H); δ 6.89, multiplet, 2H (aryl H); δ 3.71, s, 3H (—$OCH_3$); δ 3.60, s, 2H ($CH_2$).

Example 14—Preparation of 5-(4-Methoxy-phenylsulfanyl)-pentanoic acid (Compound 14)

Prepared analogously to Compound 13 with 4-methoxy-benzenthiol (2.00 mL, 16 mmol), ethyl 5-bromopentanoate (2.57 mL, 16 mmol), potassium hydroxide (1.98 g, 35 mmol) and 30 mL ethyl alcohol. The product (3.22 g, 80%) was isolated by filtration as an off-white solid. 1H NMR (d6-DMSO): δ 11.95, broad s, 1H (COOH); δ 7.26, multiplet, 2H (aryl H); δ 6.85, multiplet, 2H (aryl H); δ 3.69, s, 3H (—$OCH_3$); δ 2.78, t, 2H ($CH_2$ α to S); δ 2.15, t, 2H ($CH_2$ α to COOH); δ 1.60-1.40, multiplet, 4H (rest of $CH_2$'s).

Example 15—Preparation of 6-(4-Methoxy-phenylsulfanyl)-hexanoic acid (Compound 15)

Prepared analogously to Compound 13 with 4-methoxy-benzenthiol (2.00 mL, 16 mmol), ethyl 6-bromohexanoate (2.89 mL, 16 mmol), potassium hydroxide (1.98 g, 35 mmol) and 30 mL ethyl alcohol. The product (3.34 g, 80%) was isolated by filtration as an off-white solid. 1H NMR (d6-DMSO): (COOH); δ 7.40, multiplet, 2H (aryl H); δ 7.00, multiplet, 2H (aryl H); δ 3.83, s, 3H (—$OCH_3$); δ 2.91, t, 2H ($CH_2$ α to S); δ 2.26, t, 2H ($CH_2$ α to COOH); δ 1.65-1.40, multiplet, 6H (rest of $CH_2$'s).

Example 16—Preparation of 7-(2-Methoxy-phenylsulfanyl)-heptanoic acid (Compound 16)

Prepared analogously to Compound 6 with 2-methoxy-benzenethiol (1.4 mL, 11 mmol), ethyl 7-bromoheptanoate (2.2 mL, 11 mmol), 30 mL ethyl alcohol, potassium hydroxide (1.9 g, 34 mmol), and 25 mL water. Crude product was further purified by dissolving in 10 mL of aqueous 1 N sodium hydroxide solution and 100 mL of water and then acidifying solution to pH 1 with aqueous 1 N hydrochloric acid. Product (2.2 g, 73%) was isolated as a white powder by filtration. 1H NMR (d6-DMSO): δ 12.0, broad s, 1H (COOH); δ 7.19, dd, 1H (aryl H); δ 7.13, dt, 1H (aryl H); δ 6.9, multiplet, 2H (aryl H); δ 3.8, s, 3H ($OCH_3$); δ 2.8, t, 2H ($CH_2$ α to S); δ 2.2, 2H ($CH_2$ α to COOH); δ 1.6-1.2, complex, 8H (rest of $CH_2$'s).

Example 17—Preparation of 4-(4-Methoxy-phenylsulfanyl)-butyric acid (Compound 17)

Prepared analogously to Compound 13 with 4-methoxy-benzenthiol (2.00 mL, 16 mmol), ethyl 4-bromobutyrate (2.33 mL, 16 mmol), potassium hydroxide (1.96 g, 35 mmol) and 30 mL ethyl alcohol. The crude product was dissolved in aqueous 1 N sodium hydroxide solution (10 mL) and 10 mL water. The cloudy aqueous layer was decanted off from the insoluble viscous yellow-brown oil and was then acidified to pH 1 with aqueous 1 N hydrochloric acid. The product (2.72 g, 74%) was isolated by filtration as a white solid. 1H NMR (d6-DMSO): δ 11.95, broad s, 1H δ 12.08, s, 1H (COOH); δ 7.31, multiplet, 2H (aryl H); δ 6.91, multiplet, 2H (aryl H); δ 3.74, s, 3H (—$OCH_3$); δ 2.84, t, 2H ($CH_2$ α to S); δ 2.33, t, 2H ($CH_2$ α to COOH); δ 1.70, p, 2H (last $CH_2$).

Example 18—Preparation of 3-(4-Methoxy-phenylsulfanyl)-propionic acid (Compound 18)

Prepared analogously to Compound 17 with 4-methoxy-benzenthiol (2.50 mL, 20 mmol), ethyl 3-bromopropanoate (2.61 mL, 20 mmol), potassium hydroxide (2.39 g, 42 mmol) and 30 mL ethyl alcohol. The product (2.30 g, 53%) was isolated by filtration as an off-white solid. 1H NMR (d6-DMSO): δ 12.29, s, 1H (COOH); δ 7.33, multiplet, 2H (aryl H); δ 6.92, multiplet, 2H (aryl H); δ 3.74, s, 3H (—$OCH_3$); δ 2.99, t, 2H ($CH_2$ α to S); δ 2.44, t, 2H ($CH_2$ α to COOH).

Example 19—Preparation of 5-(2-Methoxy-phenylsulfanyl)-pentanoic acid (Compound 19)

Prepared analogously to Compound 6 with 2-methoxy-benzenethiol (1.5 mL, 12.5 mmol), ethyl 5-bromovalerate (2.0 mL, 12.5 mmol), 25 mL ethyl alcohol, potassium hydroxide (2.0 g, 37 mmol), and 15 mL water. Product (2.6 g, 87%) was isolated as a white powder by filtration. 1H NMR (d6-DMSO): δ 12.0, broad s, 1H (COOH); δ 7.2, dd, 1H (aryl H); 7.14, dt, 1H (aryl H); δ 6.9, 2H (aryl H); δ 3.8, s, 3H($OCH_3$); δ 2.85, t, 2H ($CH_2$ α to S); δ 2.2, t, 2H ($CH_2$ α to COOH); δ 1.7-1.5, complex, 4H (rest of $CH_2$'s).

Example 20—Preparation of 10-(3-Methoxy-phenylsulfanyl)-decanoic acid (Compound 20)

Prepared analogously to Compound 6 with 3-methoxy-benzenthiol (1.2 mL, 9.7 mmol), ethyl 10-bromodecanoate (2.3 mL, 9.7 mmol), 45 mL ethyl alcohol, potassium hydroxide (1.6 g, 29 mmol), and 15 mL water. Product (2.6 g, 88%)

was isolated as a white powder by filtration. 1H NMR (d6-DMSO): δ 12.0, broad s, 1H(COOH); δ 7.2, t, 1H (aryl H); δ 6.8, multiplet, 2H (aryl H); δ 6.7, dd, 1H (aryl H); δ 3.7, s, 3H (OCH$_3$); δ 2.9, t, 2H (CH$_2$ α to S); δ 2.15, t, 2H (CH$_2$ α to COOH); δ 1.6-1.1, complex, 14H (rest of CH$_2$'s).

Example 21—Preparation of 6-(3-Methoxy-phenylsulfanyl)-hexanoic acid (Compound 21)

Prepared analogously to Compound 6 with 3-methoxybenzenethiol (2.0 mL, 16 mmol), ethyl 6-bromohexanoate (2.9 mL, 16 mmol), 35 mL ethyl alcohol, potassium hydroxide (2.7 g, 49 mmol), and 20 mL water. The product (3.7 g, 89%) was isolated as a white powder by filtration. 1H NMR (d6-DMSO): δ 7.19, t, 1H (aryl H); δ 6.83, multiplet, 2H (aryl H); δ 6.71, dd, 1H (aryl H); δ 3.72, s, 3H (OCH$_3$); δ 2.92, t, 2H (CH$_2$ α to S); δ 2.15, t, 2H (CH$_2$ α to COOH); δ 1.6-1.3, complex, 6H (rest of CH$_2$'s).

Example 22—Preparation of 8-(3-Methoxy-phenylsulfanyl)-hexanoic acid (Compound 22)

Prepared analogously to Compound 6 with 3-methoxybenzenethiol (1.5 mL, 12 mmol), ethyl 8-bromooctanoate (2.6 mL, 12 mmol), 30 mL ethyl alcohol, potassium hydroxide (2.0 g, 36 mmol), and 15 mL water. Ethyl alcohol was distilled at atmospheric pressure. The crude product was further purified by dissolving in 10 mL aqueous 1 N sodium hydroxide solution and 100 mL of water. The solution was acidified to pH 1 with aqueous 1 N hydrochloric acid. The product (2.9 g, 93%) was isolated as a white solid by filtration. 1H NMR (d6-DMSO): δ 12.0, broad s, 1H (COOH); δ 7.2, t, 1H (aryl H); δ 6.83, multiplet, 2H (aryl H); δ 6.71, dd, 1H (aryl H); δ 3.72, s, 3H (OCH$_3$); δ 2.93, t, 2H (CH$_2$ α to S); δ 2.16, t, 2H (CH$_2$ α to COOH); δ 1.6-1.2, complex, 10H (rest of CH$_2$'s).

Example 23—Preparation of (3-Chloro-phenylsulfanyl)-acetic acid (Compound 23)

Prepared analogously to Compound 13 with 3-chlorobenzenethiol (2.00 mL, 17 mmol), ethyl bromoacetate (1.91 mL, 17 mmol), potassium hydroxide (3.04 g, 54 mmol) and 40 mL ethyl alcohol. Hydrolysis step used 20 mL water and 10 mL of aqueous 1 N sodium hydroxide solution and was heated to 55° C. for 5 hours. The product (3.11 g, 89%) was isolated by filtration as a white solid. 1H NMR (d6-DMSO): δ 12.85, broad s, 1H (COOH); δ 7.39, t, 1H (aryl H); δ 7.33, t, 1H (aryl H); δ 7.28, dt, 1H (aryl H); δ 7.24, dt, 1H (aryl H); δ 3.88, s, 2H (CH$_2$).

Example 24—Preparation of 5-(3-Chloro-phenylsulfanyl)-pentanoic acid (Compound 24)

Prepared analogously to Compound 23 with 3-chlorobenzenethiol (2.00 mL, 17 mmol), ethyl 5-bromopentanoate (2.72 mL, 17 mmol), potassium hydroxide (3.10 g, 55 mmol) and 30 mL ethyl alcohol. The product (3.73 g, 88%) was isolated by filtration as a white solid. 1H NMR (d6-DMSO): δ 12.85, broad s, 1H (COOH); δ 7.35, t, 1H (aryl H); δ 7.32, t, 1H (aryl H); δ 7.26, dt, 1H (aryl H); δ 7.21, dt, 1H (aryl H); δ 3.01, t, 2H (CH$_2$ α to S); δ 2.24, t, 2H (CH$_2$ α to COOH); δ 1.7-1.5, complex, 4H (rest of CH$_2$'s).

Example 25—Preparation of 5-(2-Chloro-phenylsulfanyl)-pentanoic acid (Compound 25)

Prepared analogously to Compound 23 with 2-chlorobenzenethiol (2.00 mL, 18 mmol), ethyl 5-bromopentanoate (2.80 mL, 18 mmol), potassium hydroxide (3.10 g, 55 mmol) and 30 mL ethyl alcohol. The product (3.86 g, 89%) was isolated by filtration as a white solid. 1H NMR (d6-DMSO): δ 12.03, s, 1H (COOH); δ 7.44, dd, 1H (aryl H); δ 7.38, dd, 1H (aryl H); δ 7.33, dt, 1H (aryl H); δ 7.18, dt, 1H (aryl H); δ 3.00, t, 2H (CH$_2$ α to S); δ 2.26, t, 2H (CH$_2$ α to COOH); δ 1.7-1.6, complex, 4H (rest of CH$_2$'s).

Example 26—Preparation of 6-(2-Chloro-phenylsulfanyl)-hexanoic acid (Compound 26)

Prepared analogously to Compound 23 with 2-chlorobenzenethiol (2.00 mL, 18 mmol), ethyl 5-bromopentanoate (3.14 mL, 18 mmol), potassium hydroxide (3.04 g, 54 mmol) and 30 mL ethyl alcohol. The product (4.25 g, 93%) was isolated by filtration as an off-white solid. 1H NMR (d6-DMSO): δ 11.99, s, 1H (COOH); δ 7.44, dd, 1H (aryl H); δ 7.37, dd, 1H (aryl H); δ 7.33, dt, 1H (aryl H); δ 7.17, dt, 1H (aryl H); δ 2.99, t, 2H (CH$_2$ α to S); δ 2.20, t, 2H (CH$_2$ α to COOH); δ 1.7-1.3, complex, 6H (rest of CH$_2$'s).

Example 27—Preparation of 4-(3-Methoxy-phenylsulfanyl)-butyric acid (Compound 27)

Prepared analogously to Compound 6 with 3-methoxybenzenethiol (1.7 mL, 13 mmol), ethyl 4-bromobutyrate (1.9 mL, 13 mmol), 25 mL ethyl alcohol, and potassium hydroxide (2.5 g, 44 mmol). Reaction was allowed to stir under nitrogen atmosphere for 10 days. Water (15 mL) was added and the reaction was allowed to mix for 5 hours. Ethyl alcohol was distilled off under atmospheric pressure. The residual was diluted with water (10 mL) was acidified to pH 1 with aqueous 1 N hydrochloric acid and cooled to 4° C. for 18 hours. The crude product, isolated by filtration, was further purified by dissolving in 10 mL aqueous 1 N sodium hydroxide solution and 100 mL of water. The solution was then acidified to pH 1 with aqueous 1 N hydrochloric acid and crude product collected by filtration. The crude product was then dissolved in 10 mL aqueous 1 N sodium hydroxide solution and 100 mL of water. The solution was then slowly acidified step wise to pH 7, pH 6, pH 5 and finally to pH 1 by the addition of aqueous 1 N hydrochloric acid. At each step the small amount of yellow oil that precipitated was removed via pipette. Product (1.6 g, 52%) was isolated as off-white solid by filtration. 1H NMR (d6-DMSO): δ 12.1, broad s, 1H (COOH); δ 7.17, t, 1H (aryl H); δ 6.83, multiplet, 2H (aryl H); δ 6.7, dd, 1H (aryl H); δ 3.7, s, 3H (OCH$_3$); δ 2.9, t, 2H (CH$_2$ α to S); 2.3, t, 2H (CH$_2$ α to COOH); δ 1.73, quintet, 2H (remaining CH$_2$).

Example 28—Preparation of (2-Chloro-phenylsulfanyl)-acetic acid (Compound 28)

To a mini-tube equipped with a magnetic stir bar, was added 2-chlorobenzene thiol (1.0 mL, 8.8 mmol), ethyl bromoacetate (0.98 mL, 8.8 mmol), and 35 mL ethyl alcohol. Potassium hydroxide (1.5 g, 24 mmol) was added at room temperature. Reaction was stirred at room temperature under nitrogen atmosphere for 18 hours. Water (20 mL) was added and the reaction stirred for 3 hours. Ethyl alcohol was distilled at atmospheric pressure and the residual was diluted with 100 mL of water. The solution was acidified to pH 1 with aqueous 1 N hydrochloric acid and cooled to 4° C. for 2 hours. The product (1.2 g, 61%) was isolated as white powder by filtration. 1H NMR (d6-DMSO): δ 12.9, broad s, 1H (COOH); 67.4, d, 1H (aryl H); δ 7.3, dd, 2H (aryl H); δ 7.15, multiplet, 1H (aryl H); δ 3.85, s, 2H ($CH_2$).

Example 29—Preparation of
4-(3-Chloro-phenylsulfanyl)-butyric acid
(Compound 29)

Prepared analogously to Compound 23 with 3-chlorobenzenethiol (2.00 mL, 17 mmol), ethyl 4-bromobutyrate (2.47 mL, 17 mmol), potassium hydroxide (3.03 g, 54 mmol) and 30 mL ethyl alcohol. The crude product was further purified by dissolving in 20 mL of aqueous 1 N sodium hydroxide solution and 30 mL water. The solution was acidified to pH 1 with aqueous 1 N hydrochloric acid. The product (2.99 g, 75%) was isolated by filtration as a brownish solid. 1H NMR (d6-DMSO): δ 12.85, broad s, 1H (COOH); δ 7.37, t, 1H (aryl H); δ 7.32, t, 1H (aryl H); δ 7.27, dt, 1H (aryl H); δ 7.22, dt, 1H (aryl H); δ 3.01, t, 2H ($CH_2$ α to S); δ 2.35, t, 2H ($CH_2$ α to COOH); δ 1.77, pentet, 2H (other $CH_2$'s).

Example 30—Preparation of
8-(2-Chloro-phenylsulfanyl)-octanoic acid
(Compound 30)

To a mini-tube equipped with a magnetic stir bar, was added 2-chlorobenzene thiol (1.0 mL, 8.2 mmol), ethyl 8-bromooctanoate (1.8 mL, 8.2 mmol), and 45 mL ethyl alcohol. Potassium hydroxide (1.5 g, 26 mmol) was added at room temperature and the reaction was allowed to stir at room temperature for 1 hr under a nitrogen atmosphere. Water (10 mL) was added and the stirring continued for 3 hours. The reaction was heated to 45° C. for 0.5 hr, cooled to room temperature and stirred for an additional 96 hours. Solvent was removed under reduced pressure and the resulting solution was acidified to pH 1 with aqueous 1 N hydrochloric acid and cooled to 4° C. for 45 min. Product (2.24 g, 88%) was isolated as a white powder by filtration. 1H NMR (d6-DMSO): δ 11.96, broad s, 1H (COOH); δ 7.42, dd, 1H (aryl H); δ 7.33, multiplet, 2H (aryl H); δ 7.16, dt, 1H (aryl H); δ 2.97, t, 2H ($CH_2$ α to S); δ 2.17, t, ($CH_2$ α to COOH); δ 1.6-1.25, complex, 10H (rest of $CH_2$'s).

Example 31—Preparation of
4-(2-Chloro-phenylsulfanyl)-butyric acid
(Compound 31)

Prepared analogously to Compound 30 with 2-chlorobenzenethiol (1 mL, 8.2 mmol), ethyl 4-bromobutyrate (1.3 mL, 8.2 mmol), 45 mL ethyl alcohol, and potassium hydroxide (1.5 g, 27 mmol). The product (0.92 g, 45%) was isolated by filtration as a white powder. 1H NMR (d6-DMSO): δ 12.1, broad s, 1H (COOH); δ 7.38, multiplet, 2H (aryl H); δ 7.27, dt, 1H (aryl H); δ 7.12, dt, 1H (aryl H); δ 2.96, t, 2H ($CH_2$ α to S); δ 2.33, t, 2H ($CH_2$ α to COOH); δ 1.75, quintet, 2H (remaining $CH_2$).

Example 32—Preparation of
6-(3-Chloro-phenylsulfanyl)-hexanoic acid
(Compound 32)

Prepared analogously to Compound 30 with 3-chlorobenzenethiol (1.0 mL, 8.6 mmol), ethyl 6-bromohexanoate (1.5 mL, 8.6 mmol), 45 mL ethyl alcohol, and potassium hydroxide (1.5 g, 26 mmol). The product (1.9 g, 84%) was isolated by filtration as a white powder. 1H NMR (d6-DMSO): δ 11.94, broad s, 1H (COOH); δ 7.28, t, 1H (aryl H); δ 7.26, d, 1H (aryl H); δ 7.2, dt, 1H (aryl H); δ 7.16, dt, 1H (aryl H); δ 2.95, t, 2H ($CH_2$ α to S); δ 2.14, t, 2H ($CH_2$ α to COOH); 61.55-1.3, complex, 6H (rest of $CH_2$'s).

Example 33—Preparation of
8-(4-Chloro-phenylsulfanyl)-octanoic acid
(Compound 33)

To a 250 mL round bottom flask, equipped with a magnetic stir bar, was added 4-chlorobenzenethiol (5.00 g, 35 mmol), ethyl 8-bromooctanoate (8.68 g, 35 mmol), potassium hydroxide (3.87 g, 69 mmol), and 100 mL methylene chloride. The mixture was stirred at room temperature for 24 hours. The solvent was removed by filtration and the resulting solid was dissolved in 150 mL water. The solution was adjusted to pH 7 with aqueous 1 N hydrochloric acid. The precipitate which formed was collected by filtration and washed with water (2×50 mL) yielding the product (0.20 g, 2%) as an off-white solid, mp 92-93° C. Found: C: 58.55%, H: 6.61% S: 11.41%, Cl: 12.01%; $C_{14}H_{19}ClO_2S$ requires C: 58.63%, H: 6.68%, S: 11.18%, Cl: 12.36%; 1H NMR (d6-DMSO): δ 7.35, multiplet, 4H (aryl H's); δ 2.95, t, 2H ($CH_2$ α to S); δ 2.15, t, 2H ($CH_2$ α to COOH); δ 1.7-1.1, multiplet, 10H (rest of $CH_2$'s).

Example 34—Preparation of
4-(4-Chloro-phenylsulfanyl)-butyric acid
(Compound 34)

To a 250 mL round bottom flask, equipped with a magnetic stir bar, was added 4-chlorobenzenethiol (5.00 g, 35 mmol), 4-bromobutyric acid (5.77 g, 35 mmol), potassium hydroxide (1.94 g, 35 mmol), and 100 mL tetrahydrofuran. The mixture was stirred at room temperature for 48 hours. The reaction mixture was filtered to remove solid byproducts and the solvent was removed under reduced pressure. Crystallization from methyl alcohol:water (3:1) yielded the product (2.10 g, 26%) as an off-white solid, mp 100-101° C. Found: C: 52.17%, H: 4.75% S: 13.53%, Cl: 15.28%; $C_{10}H_{11}ClO_2S$ requires C: 52.05%, H: 4.81%, S: 13.89%, Cl: 15.37%; 1H NMR (d6-DMSO): δ 7.35, multiplet, 4H (aryl H's); δ 3.00, t, 2H ($CH_2$ α to S); δ 2.40, t, 2H ($CH_2$ α to COOH); δ 1.75, multiplet, 2H (other $CH_2$).

Example 35—Preparation of
6-(4-Hydroxy-phenylsulfanyl)-hexanoic acid
(Compound 35)

To a 125 mL round bottom flask, equipped with a magnetic stir bar, was added 4-hydroxybenzenethiol (5.00 g, 40 mmol), 6-bromohexanoic acid (7.73 g, 40 mmol), triethylamine (11.08 mL, 79 mmol), and 30 mL tetrahydrofuran. The reaction was stirred at room temperature for 96 hours. The solvent was removed under reduced pressure. The residual was dissolved in water (100 mL) and acidified with aqueous 1 N hydrochloric acid solution to pH 2. The precipitate was collected by filtration. Recrystallization from acetonitrile/water yielded the product (3.10 g, 33%) as an off-white solid, mp 92-94° C. Found: C: 59.88%, H: 6.62% S: 13.23%; $C_{12}H_{16}O_3S$ requires C: 59.97%, H: 6.71%, S: 13.34%; 1H NMR (d6-DMSO): δ 7.20, multiplet, 2H (aryl H's); δ 6.75, multiplet, 2H (aryl H's); δ 2.80, t, 2H (CH$_2$ α to S); δ 2.20, t, 2H (CH$_2$ α to COOH); δ 1.7-1.3, multiplet, 6H (rest of CH$_2$'s).

Example 36—Preparation of
4-(3-Hydroxy-phenylsulfanyl)-butyric acid
(Compound 36)

To a mini-tube equipped with a magnetic stir bar, was added 3-mercaptophenol (0.96 mL, 9.4 mmol), 15 mL ethyl alcohol, 5 mL water, and potassium carbonate (1.6 g, 12 mmol). Ethyl 4-bromobutyrate (1.35 mL, 9.4 mmol) was added drop-wise and the reaction was allowed to stir at room temperature under a nitrogen atmosphere for 20 minutes. Aqueous 1 N sodium hydroxide solution (28 mL) was added and the reaction was allowed to stir at room temperature for 18 hours. The mixture was heated to 45° C. for 3 hours, cooled to room temperature and stirred under a nitrogen atmosphere for 48 hours. Ethyl alcohol was distilled at atmospheric pressure and the residue was dissolved in aqueous 1 N sodium hydroxide solution (10 mL) and diluted with 100 mL water. The solution was acidified to pH 1 with aqueous 1 N hydrochloric acid and cooled to 4° C. for 1 hr. The product (1.4 g, 72%) was isolated as a tan solid by filtration. 1H NMR (d6-DMSO): δ 12.0, broad s, 1H (COOH); δ 9.5, broad s, 1H (Ar—OH); δ 7.1, t, 1H (aryl H); δ 6.7, multiplet, 2H (aryl H); δ 6.5, dd, 1H (aryl H); δ 2.9, t, 2H (CH$_2$ α to S); δ 2.3, t, 2H (CH$_2$ α to COOH); δ 1.75, quintet, 2H (remaining of CH$_2$'s).

Example 37—Preparation of
8-(3-Hydroxy-phenylsulfanyl)-octanoic acid
(Compound 37)

Prepared analogously to Compound 36 with 3-mercaptophenol (0.85 mL, 8.3 mmol), potassium carbonate (1.4 g, 10.4 mmol), ethyl 8-bromooctanoate (1.75 mL, 8.3 mmol), 15 mL ethyl alcohol, and 5 mL water for first step of reaction. Aqueous 1 N sodium hydroxide (25 mL, 25 mmol) was used for second reaction step. Crude product was further purified by dissolving in 10 mL aqueous 1 N sodium hydroxide solution and 100 mL water. The solution was then acidified to pH 1 with aqueous 1 N hydrochloric acid and cooled to 4° C. for 18 hours. Product (1.9 g, 84%) was isolated as an off-white powder by filtration. 1H NMR (d6-DMSO): δ 7.3, t, 1H (aryl H); δ 6.65, multiplet, 2H (aryl H); δ 6.5, dd, 1H (aryl H), 62.8, t, 2H (CH$_2$ α to S); δ 2.1, t, 2H (CH$_2$ α to COOH); δ 1.5-1.2, complex, 10H (rest of CH$_2$'s).

Example 38—Preparation of
10-(4-Hydroxy-phenylsulfanyl)-decanoic acid
(Compound 38)

Prepared analogously to Compound 36 with 4-hydroxythiophenol (0.76 mL, 6.8 mmol), potassium carbonate (3.7 g, 27 mmol), ethyl 10-bromodecanoate (1.6 mL, 6.8 mmol), 15 mL ethyl alcohol, and 5 mL water for first step of reaction. Aqueous 10 N sodium hydroxide solution (2.0 mL, 20 mmol) was used for second reaction step. The product (1.26 g, 63%) was isolated as a tan solid by filtration. 1H NMR (deuterium oxide with NaOD added): δ 7.0, multiplet, 2H (aryl H); δ 6.4, multiplet, 2H (aryl H); δ 2.6, broad t, 2H (CH$_2$ α to S); δ 1.95, broad t, 2H (CH$_2$ α to COOH); δ 2.0-1.0, complex, 14H (rest of CH$_2$'s).

Example 39—Preparation of
10-(3-Hydroxy-phenylsulfanyl)-decanoic acid
(Compound 39)

Prepared analogously to Compound 36 with 3-mercaptophenol (0.85 mL, 8.3 mmol), potassium carbonate (1.4 g, 10 mmol), ethyl 10-bromodecanoate (2.0 mL, 8.3 mmol), 15 mL ethyl alcohol, and 5 mL water for first step of reaction. Aqueous 1 N sodium hydroxide solution (25 mL, 25 mmol) was used for second reaction step. The crude product was further purified by dissolving in 10 mL of aqueous 1 N sodium hydroxide solution and 100 mL water. The solution was acidified to pH 1 with aqueous 1 N hydrochloric acid and cooled to 4° C. for 3 hours. Product (2.1 g, 85%) was isolated an off-white solid by filtration. 1H NMR (d6-DMSO): δ7.0, t, 1H (aryl H); δ6.64, multiplet, 2H (aryl H); δ 6.5, dd, 1H (aryl H); δ 2.83, t, 2H (CH$_2$ α to S); δ2.1, t, 2H (CH$_2$ α to COOH); δ1.5-1.1, complex, 10H (rest of CH$_2$'s).

Example 40—Preparation of
(2,5-dichloro-phenylsulfanyl)-acetic acid
(Compound 40)

To a mini-tube equipped with a magnetic stir bar, was added 2,5-dichlorobenzenethiol (1.1 mL, 8.3 mmol), 20 mL ethyl alcohol, 10 mL water, and potassium hydroxide (1.4 g, 25 mmol). The reaction was stirred under a nitrogen atmosphere for 20 mm then ethyl bromoacetate (0.92 mL, 8.3 mmol) was added. The reaction was heated to 45° C. for 1 hour. Ethyl alcohol (5 mL) and water (2 mL) were added to dissolve formed precipitate and the reaction was allowed to stir for 48 hours. Ethyl alcohol was distilled at atmospheric pressure and the residue was dissolved in aqueous 1 N sodium hydroxide solution (10 mL) and diluted with 100 mL water. The solution was acidified to pH 1 with aqueous 1 N hydrochloric acid and cooled to 4° C. for 3 days. Product (1.7 g, 88%) was isolated as a white powder by filtration. 1H NMR (d6-DMSO): δ7.46, d, 1H (aryl H); δ 7.35, d, 1H (aryl H); δ 7.23, dd, 1H (aryl H); δ 4.0, s, 2H (CH$_2$).

Example 41—Preparation of
6-(2,5-dichloro-phenylsulfanyl)-hexanoic acid
(Compound 41)

Prepared analogously to Compound 40 with 2,5-dichlorobenzenethiol (1.1 mL, 8.3 mmol), potassium hydroxide (1.4 g, 25 mmol), 20 mL ethyl alcohol, 10 mL water, and ethyl 6-bromohexanoate (1.5 mL, 8.3 mmol). Precipitate did not form during initial reaction step; extra ethyl alcohol and water were not required. Product (2.1 g, 88%) was isolated as a white powder by filtration. 1H NMR (d6-DMOS): δ11.9, broad s, 1H (COOH); δ7.4, d, 1H (aryl H); δ7.28, d, 1H (aryl H); δ7.14, dd, 1H (aryl H); δ2.95, t, 2H (CH$_2$ α to S); δ 2.1, t, 2H (CH$_2$ α to COOH); δ1.6-1.3, complex, 6H (rest of CH$_2$'s).

Example 42—Preparation of
(3,4-dichloro-phenylsulfanyl)-acetic acid
(Compound 42)

Prepared analogously to Compound 40 with 3,4-dichlorobenzenethiol (1.1 mL, 8.3 mmol), potassium hydroxide (1.4 g, 25 mmol), 20 mL ethyl alcohol, 10 mL water, and ethyl bromoacetate (0.92 mL, 8.3 mmol). Precipitate did not form during initial reaction step; extra ethyl alcohol and water were not required. Product (1.6 g, 83%) was isolated as a white powder by filtration. 1H NMR (d6-DMSO): δ 12.9, broad s, 1H (COOH); δ 7.55, d, 1H (aryl H); δ 7.51, d, 1H (aryl H); δ 7.27, dd, 1H (aryl H); δ 3.9, s, 2H (CH$_2$).

Example 43—Preparation of 6-(3,4-dichloro-phenylsulfanyl)-hexanoic acid (Compound 43)

Prepared analogously to Compound 40 with 3,4-dichlorobenzenethiol (1.1 mL, 8.3 mmol), potassium hydroxide (1.4 g, 25 mmol), 20 mL ethyl alcohol, 10 mL water, and ethyl 6-bromohexanoate (1.5 mL, 8.3 mmol). Precipitate did not form during initial reaction step; extra ethyl alcohol and water were not required. Product (0.75 g, 31%) was isolated as a white solid by filtration. 1H NMR (d6-DMSO): δ 11.9, s, 1H (COOH); δ 7.5, multiplet, 2H (aryl H); δ 7.2, dd, 1H (aryl H); δ 2.95, t, 2H (CH$_2$ α to S); δ 2.15, t, 2H (CH$_2$ α to COOH); δ 1.6-1.3, 6H (rest of CH$_2$'s).

Example 44—Preparation of 3-(2-Chloro-phenylsulfanyl)-propionic acid (Compound 44)

To a 500 mL round bottom flask, equipped with a magnetic stir bar, was added 2-chlorobenzenethiol (2.00 mL, 18 mmol), ethyl 3-bromopropionate (2.26 mL, 18 mmol), potassium hydroxide (2.08 g, 37 mmol), and 50 mL ethyl alcohol. The reaction mixture was stirred at room temperature for 4 hours, 15 mL water was added and the mixture was stirred for 42 hours at room temperature. Ethyl 3-bromopropionate (1.70 mL, 13 mmol) and potassium hydroxide (2.19 g, 39 mmol) were added in three aliquots during the next 18 hours. Solvent was removed under reduced pressure. Residual was dissolved in 150 mL water and acidified with aqueous 1 N hydrochloric acid solution to pH 1. Filtration yielded the product (3.56 g, 93%) as a white solid. 1H NMR (d6-DMSO): δ 12.41, s, 1H (COOH); δ 7.46, dd, 1H (aryl H); δ 7.40, dd, 1H (aryl H); δ 7.34, dt, 1H (aryl H); δ 7.20, dt, 1H (aryl H); δ 3.18, t, 2H (CH$_2$ α to S); δ 2.59, t, 2H (CH$_2$ α to COOH).

Example 45—Preparation of 3-(3-Chloro-phenylsulfanyl)-propionic acid (Compound 45)

Prepared analogously to Compound 44, with 3-chlorobenzenethiol (2.0 mL, 17 mmol), ethyl 3-bromopropionate (2.21 mL, 17 mmol), potassium hydroxide (2.01 g, 36 mmol), 50 mL ethyl alcohol. For aliquots: ethyl 3-bromopropionate (1.70 mL, 13 mmol) and potassium hydroxide (2.22 g, 39 mmol) were used. Filtration yielded the product (3.24 g, 88%) as a white solid. 1H NMR (d6-DMSO): δ 12.38, s, 1H (COOH); δ 7.38, t, 1H (aryl H); δ 7.34, t, 1H (aryl H); δ 7.28, dt, 1H (aryl H); δ 7.24, dt, 1H (aryl H); δ 3.18, t, 2H (CH$_2$ α to S); δ 2.55, t, 2H (CH$_2$ α to COOH).

Example 46—Preparation of (3-Hydroxy-phenylsulfanyl)-acetic acid (Compound 46)

Prepared analogously to Compound 36 with 3-mercaptophenol (1.1 mL, 11 mmol), potassium carbonate (1.9 g, 14 mmol), and ethyl bromoacetate (1.2 mL, 11 mmol). Product did not precipitate from acidic solution. Aqueous acid solution was extracted with ethyl acetate (3×50 mL). Combined organic layers were dried over anhydrous sodium sulfate, filtered to remove drying agent and solvent removed under reduced pressure. Residual acetic acid was removed by azeotroping with toluene (4×100 mL) to yield the product (1.4 g, 70%) as a tan solid. 1H NMR (d6-Acetone): δ 7.1, t, 1H (aryl H); δ 6.8, multiplet, 2H (aryl H); δ 6.6, dd, 1H (aryl H); δ 3.7, s, 2H (CH$_2$).

Example 47—Preparation of (2-Fluoro-phenylsulfanyl)-acetic acid (Compound 47)

Prepared analogously to Compound 40 with 2-fluorothiophenol (1.2 mL, 11 mmol), potassium hydroxide (1.8 g, 32 mmol), 20 mL ethyl alcohol, 10 mL water, and ethyl bromoacetate (1.2 mL, 11 mmol). Product (1.3 g, 67%) was isolated as a white powder by filtration. 1H NMR (d6-DMSO): δ 13.0, s, 1H (COOH); δ 7.38, dt, 1H (aryl H); δ 7.25-7.1, multiplet, 3H (aryl H); δ 3.8, s, 2H (CH$_2$).

Example 48—Preparation of 6-(2-Fluoro-phenylsulfanyl)-hexanoic acid (Compound 48)

Prepared analogously to Compound 40 with 2-fluorothiophenol (0.88 mL, 8.2 mmol), potassium hydroxide (1.4 g, 25 mmol), 20 mL ethyl alcohol, 10 mL water, and ethyl 6-bromohexanoate (1.5 mL, 8.2 mmol). Product (1.8 g, 88%) was isolated as a white powder by filtration. 1H NMR (d6-DMSO): δ 12.0, s, 1H (COOH); δ 7.4, dt, 1H (aryl H); δ 7.25-7.1, multiplet, 3H (aryl H); δ 2.9, t, 2H (CH$_2$ α to S); δ 2.1, t, 2H (CH$_2$ α to COOH); δ 1.6-1.3, complex, 6H (rest of CH$_2$'s).

Example 49—Preparation of 6-(3-Fluoro-phenylsulfanyl)-hexanoic acid (Compound 49)

Prepared analogously to Compound 40 with 3-fluorothiophenol (0.70 mL, 8.3 mmol), potassium hydroxide (1.4 g, 25 mmol), 20 mL ethyl alcohol, 10 mL water, and ethyl 6-bromohexanoate (1.5 mL, 8.3 mmol). Product (1.4 g, 70%) was isolated as a white solid by filtration. 1H NMR (d6-DMSO): δ 12.0, s, 1H (COOH); δ 7.3. dt, 1H (aryl H); δ 7.1, dt, 2H (aryl H); δ 6.9, dt, 1H (aryl H); δ 3.0, t, 2H (CH$_2$ α to S); δ 2.1, t, 2H (CH$_2$ α to COOH); δ 1.6-1.3, complex, 6H (rest of CH$_2$'s).

Example 50—Preparation of 4-(2,5-dichloro-phenylsulfanyl)-butyric acid (Compound 50)

Prepared analogously to Compound 40 with 2,5-dichlorobenzenethiol (1.1 mL, 8.3 mmol), potassium hydroxide (1.4 g, 25 mmol), 20 mL ethyl alcohol, 10 mL water, and ethyl 4-bromobutyrate (1.2 mL, 8.3 mmol). Reaction was allowed to stir for 8 days under nitrogen atmosphere. Crude product was further purified by dissolving in 3 mL ethyl alcohol and 8 mL aqueous 1 N sodium hydroxide and allowing to stir under nitrogen atmosphere for 48 hours. The solution was acidified to pH 1 with aqueous 1 N hydrochloric acid and cooled to 4° C. for 4 days. The product (0.49 g, 22%) was isolated as a white solid by filtration. 1H NMR (d6-DMSO): δ 12.2, s, 1H (COOH); δ 7.4, multiplet, 2H (aryl H); δ 7.2, dd, 1H (aryl H); δ 3.0, t, 2H (CH$_2$ α to S); δ 2.35, t, 2H (CH$_2$ α to COOH); δ 1.8, quintet, 2H (remaining CH$_2$).

Example 51—Preparation of (3-Fluoro-phenylsulfanyl)-acetic acid (Compound 51)

Prepared analogously to Compound 40 with 3-fluorothiophenol (0.9 mL, 11 mmol), potassium hydroxide (1.8 g, 32 mmol), 20 mL ethyl alcohol, 10 mL water, and ethyl bromoacetate (1.2 mL, 11 mmol). The product (0.74 g, 37%) was isolated as a white powder by filtration. 1H NMR (d6-DMSO): δ 13.0, broad s, 1H (COOH); δ 7.3, dt, 1H (aryl H); δ 7.13, multiplet, 2H (aryl H); δ 6.96, dt, 1H (aryl H); δ 3.9, s, 2H (CH$_2$).

Example 52—Preparation of 4-(3-Fluoro-phenylsulfanyl)-butyric acid (Compound 52)

Prepared analogously to Compound 40 with 3-fluorothiophenol (0.8 mL, 9.4 mmol), potassium hydroxide (1.6 g, 28 mmol), 20 mL ethyl alcohol, 10 mL water, and ethyl 4-bromobutyrate (1.5 mL, 11 mmol). After stirring under a nitrogen atmosphere for 4 days, a second portion of potassium hydroxide (0.5 g, 9.4 mmol) was added and stirring under a nitrogen atmosphere continued for an additional 18 hours. The product (0.94 g, 47%) was isolated as a white solid by filtration. 1H NMR (d6-DMSO): δ 12.0, s, 1H (COOH); δ 7.25, dt, 1H (aryl H); δ 7.1, multiplet, 2H (aryl H); δ 6.9, dt, 1H (aryl H); 2.9, t, 2H (CH$_2$ α to S); δ 2.9, t, 2H (CH$_2$ α to COOH); δ 1.7, quintet, 2H (remaining CH$_2$).

Example 53—Preparation of 4-(3,4-dichloro-phenylsulfanyl)-butyric acid (Compound 53)

Prepared analogously to Compound 50 with 3,4-dichlorobenzenethiol (1.1 mL, 8.3 mmol), potassium hydroxide (1.4 g, 25 mmol), 20 mL ethyl alcohol, 10 mL water, and ethyl 4-bromobutyrate (1.2 mL, 8.3 mmol). The crude product was further purified by dissolving in 50 mL aqueous 1 N sodium hydroxide, washing aqueous solution with diethyl ether (3×25 mL), acidifying to pH 1 with aqueous 6 N hydrochloric acid and extracting with diethyl ether (3×25 mL). The organic layers were combined, dried over anhydrous sodium sulfate, filtered to remove drying agent and the solvent removed under reduced pressure. The residue was dissolved in aqueous 1 N sodium hydroxide (10 mL), diluted with water (100 mL), acidified to pH 1 using aqueous 1 N hydrochloric acid, and cooled to 4° C. for 18 hours. The product (0.73 g, 33%) was isolated as a white powder by filtration. 1H NMR (d6-DMSO): δ 12.0, broad s, 1H (COOH); δ 7.54, d, 1H (aryl H); δ 7.49, d, 1H (aryl H); δ 7.25, dd, 1H (aryl H); δ 3.0, t, 2H (CH$_2$ α to S); δ 2.3, t, 2H (CH$_2$ α to COOH); δ 1.73, quintet, 2H (remaining CH$_2$).

Example 54—Preparation of 4-(2-Fluoro-phenylsulfanyl)-butyric acid (Compound 54)

Prepared analogously to Compound 53 with 2-fluorothiophenol (1.0 mL, 9.4 mmol), potassium hydroxide (1.6 g, 28 mmol), 20 mL ethyl alcohol, 10 mL water, and ethyl 4-bromobutyrate (1.5 mL, 11 mmol). Crude oily product was further purified by dissolving in 40 mL diethyl ether, adding silica-bound maleimide (1.1 g, 14 mmol), and stirring under a nitrogen atmosphere for 20 hours. The silica-bound maleimide scavenger was removed by filtration. The solution was extracted with aqueous 1 N sodium hydroxide solution (2×50 mL). The combined aqueous layers were washed with diethyl ether (2×50 mL), acidified to pH 1 with aqueous 6 N hydrochloric acid, and extracted with diethyl ether (2×50 mL). Combined organic layers were dried over anhydrous sodium sulfate, filtered to remove drying agent, and the solvent removed under reduced pressure to yield the product (0.93 g, 46%) as an off-white solid. 1H NMR (d6-DMSO): δ 12.0, s, 1H (COOH); δ 7.4, dt, 1H (aryl H); δ 7.26-7.1, multiplet, 3H (aryl H); δ 2.9, t, 2H (CH$_2$ α to COOH); δ 2.3, t, 2H (CH$_2$ α to COOH); 1.7, quintet, 2H (remaining CH$_2$).

Example 55—Preparation of (4-Fluoro-phenylsulfanyl)-acetic acid (Compound 55)

Prepared analogously to Compound 40 with 4-fluorothiophenol (1.15 mL, 11 mmol), potassium hydroxide (1.8 g, 32 mmol), 20 mL ethyl alcohol, 5 mL water, and ethyl bromoacetate (1.2 mL, 11 mmol). The product (1.4 g, 70%) was isolated as a white powder by filtration. 1H NMR (d6-DMSO): δ 12.7, s, 1H (COOH); δ 7.4, complex, 2H (aryl); δ 7.17, dt, 2H (aryl); δ 3.75, s, 2H (CH$_2$).

Example 56—Preparation of 4-(4-Fluoro-phenylsulfanyl-butyric acid (Compound 56)

Prepared analogously to Compound 40 with 4-fluorothiophenol (1.0 mL, 9.4 mmol), potassium hydroxide (1.6 g, 28 mmol), 20 mL ethyl alcohol, 5 mL water, and ethyl 4-bromobutyrate (1.5 mL, 11 mmol). The reaction was allowed to stir under a nitrogen atmosphere for 18 hours, then potassium hydroxide (0.6 g, 10 mmol) was added and the stirring continued for an additional 48 hours. Ethyl 4-bromobutyrate (0.39 mL, 3 mmol) was added and the reaction was heated to 45° C. for 90 minutes. The reaction was cooled to room temperature and allowed to mix under a nitrogen atmosphere for 18 hours. The ethyl alcohol was removed under reduced pressure and the residue was dissolved in aqueous 1 N sodium hydroxide (10 mL) and diluted with water (100 mL). The solution was acidified to pH 1 using aqueous 1 N aqueous hydrochloric acid and cooled to 4° C. for 18 hours. Filtration yielded the product (1.2 g, 61%) as an off-white powder. 1H NMR (d-DMSO): δ 12.0, broad s, 1H (COOH); δ 7.35, complex, 2H (aryl); δ 7.13, dt, 2H (aryl); δ 2.9, t, 2H (CH$_2$ α to S); δ 2.3, t, 2H (CH$_2$ α to COOH); δ 1.7, quintet, 2H (remaining CH$_2$).

Example 57—Preparation of 6-(4-Fluoro-phenylsulfanyl)-hexanoic acid (Compound 57)

Prepared analogously to Compound 40 with 4-fluorothiophenol (0.88 mL, 8.2 mmol), potassium hydroxide (1.4 g, 24 mmol), 20 mL ethyl alcohol, 5 mL water, and ethyl 6-bromohexanoate (1.5 mL, 8.2 mmol). Filtration yielded the product (1.8 g, 88%) as a white powder. 1H NMR (d6-DMSO): δ 12.0, s, 1H (COOH); δ 7.37, complex, 2H (aryl); δ 7.15, dt, 2H (aryl); δ 2.9, t, 2H (CH$_2$ α to S); δ 2.17, t, 2H (CH$_2$ α to COOH); δ 1.6-1.3, complex, 6H (rest of CH$_2$'s).

Example 58—Preparation of (2,5-Dimethyl-phenylsulfanyl)-acetic acid (Compound 58)

To a 250 mL round bottom flask equipped with a magnetic stir bar was added 2,5-dimethylbenzenethiol (3.5 mL, 25.8 mmol), ethyl bromoacetate (4.32 mL, 25.9 mmol), and 100 mL ethanol. Potassium hydroxide (4.44 g, 79.1 mmol) was added and allowed reaction to mix under nitrogen atmosphere for 18 hours. Water (50 mL) was added and the reaction was allowed to stir for another 18 hours under nitrogen atmosphere. Ethanol was removed under reduced pressure. The remaining solution was diluted with water, acidified to pH 1 with aqueous 1N hydrochloric acid, and sonicated to form solid precipitate. The solution was cooled to 4° C. for 18 hours. Filtered to collect crude product and re-suspended in 1.0N sodium hydroxide. Acidified solution with 1N hydrochloric acid to pH 4.5 and sonicated to form a precipitate. Continued adding 1N hydrochloric acid until pH 1. Solution was cooled to 4° C. for 2-3 hours. Product (4.44 g, 88%) was isolated by filtration as a gel, mp 73-74° C. Found: C: 61.18%, H: 6.34%, S: 16.26%; $C_{10}H_{12}O_2S$ requires C: 61.2%, H: 6.16%, S: 16.34%; 1H NMR (d6-DMSO): (COOH, not visible due to water in sample); δ 7.09, d, 1H (aryl H); δ 7.06, s, 1H (aryl H); δ 6.91, dd, 1H (aryl H); δ 3.75, s, 2H ($CH_2$); δ 2.24, s, 6H (aryl-$CH_3$'s).

Example 59—Preparation of 4-(2-Chloro-phenylsulfanylmethyl)-benzoic acid (Compound 59)

Prepared analogously to Compound 33, but with 2-chloro-benzenethiol, 4-bromomethyl-benzoic acid, potassium hydroxide, and 100 mL methylene chloride. The precipitate which formed was collected by filtration and washed with water (2×50 mL) yielding the product. Found: C: 60.14%, H: 3.97% S: 11.42%, Cl: 12.73%. $C_{14}H_{11}O_2SCl$ requires C: 60.32%, H: 3.98%, S: 11.50%, Cl: 12.71%.

Example 60—Preparation of [4-(2-Methoxy-phenylsulfanylmethyl)-phenyl]-acetic acid (Compound 60)

Prepared analogously to Compound 33, but with 2-methoxy-benzenethiol, (4-bromomethyl-phenyl)-acetic acid, potassium hydroxide, and 100 mL methylene chloride. The precipitate which formed was collected by filtration and washed with water (2×50 mL) yielding the product. Found: C: 66.55%, H: 5.41% S: 11.07%; $C_{16}H_{16}O_3S$ requires C: 66.64%, H: 5.59%, S: 11.12%.

Example 61—Preparation of 4-(2-Methoxy-phenylsulfanylmethyl)-benzoic acid (Compound 61)

Prepared analogously to Compound 33, but with 2-methoxy-benzenethiol, 4-Bromomethyl-benzoic acid, potassium hydroxide, and 100 mL methylene chloride. The precipitate which formed was collected by filtration and washed with water (2×50 mL) yielding the product. Found: C: 65.66%, H: 5.13% S: 11.40%; $C_{15}H_{14}O_3S$ requires C: 65.67%, H: 5.14%, S: 11.69%.

Example 62—Preparation of (4-Phenylsulfanylmethyl-phenyl)-acetic acid (Compound 62)

Prepared analogously to Compound 33, but with benzenethiol, (4-bromomethyl-phenyl)-acetic acid, potassium hydroxide, and 100 mL methylene chloride. The precipitate which formed was collected by filtration and washed with water (2×50 mL) yielding the product. Found: C: 69.53%, H: 5.37% S: 12.51%; $C_{15}H_{14}O_2S$ requires C: 69.74%, H: 5.46%, S: 12.41%.

Example 63—Preparation of 4-Phenylsulfanylmethyl-benzoic acid (Compound 63)

Prepared analogously to Compound 33, but with Benzenethiol, 4-Bromomethyl-benzoic acid, potassium hydroxide, and 100 mL methylene chloride. The precipitate which formed was collected by filtration and washed with water (2×50 mL) yielding the product. Found: C: 68.06%, H: 4.91% S: 12.67%; $C_{14}H_{12}O_2S$ requires C: 68.73%, H: 4.95%, S: 13.11%.

Example 64—Preparation of 4-(4-Chloro-phenylsulfanylmethyl)-benzoic acid (Compound 64)

Prepared analogously to Compound 33, but with 4-chloro-benzenethiol, 4-bromomethyl-benzoic acid, potassium hydroxide, and 100 mL methylene chloride. The precipitate which formed was collected by filtration and washed with water (2×50 mL) yielding the product. Found: C: 59.90%, H: 3.92% S: 11.30%, Cl: 12.70%; $C_{14}H_{11}O_2SCl$ requires C: 60.32%, H: 3.98%, S: 11.50%, Cl: 12.72%.

Example 65—Preparation of 4-(2-Hydroxy-phenylsulfanylmethyl)-benzoic acid (Compound 65)

Prepared analogously to Compound 33, but with 2-mercapto-phenol, 4-Bromomethyl-benzoic acid, potassium hydroxide, and 100 mL methylene chloride. The precipitate which formed was collected by filtration and washed with water (2×50 mL) yielding the product. Found: C: 64.75%, H: 4.88% S: 11.96%; $C_{14}H_{12}O_3S$ requires C: 64.60%, H: 4.65%, S: 12.32%.

Example 66—Preparation of 4-(2-Hydroxy-phenylsulfanylmethyl)-benzoic acid (Compound 66)

Prepared analogously to Compound 33, but with 2-mercapto-phenol, (4-bromomethyl-phenyl)-acetic acid, potassium hydroxide, and 100 mL methylene chloride. The precipitate which formed was collected by filtration and washed with water (2×50 mL) yielding the product. Found: C: 65.41%, H: 5.07% S: 11.92%; $C_{15}H_{14}O_3S$ requires C: 65.67%, H: 5.14%, S: 11.69%.

Example 67—Oral Delivery of Insulin to Male Sprague-Dawley Rats

Insulin stock solution (15 mg/ml) (Human zinc insulin, Calbiochem-Novabiochem Corp., La Jolla, Calif.) was prepared with deionized water. Oral dosing compositions containing 200 mg/kg of delivery agent compound and 0.5 mg/kg of insulin in aqueous solution were prepared with the delivery agent compound shown in Table 1 below. Either the sodium salt of the delivery agent compound was used or the free acid was converted to the sodium salt with one equivalent of sodium hydroxide.

The dosing solution was administered to fasted male Sprague-Dawley rats by oral gavage with an average weight of about 225-250 grams. Blood glucose levels were then determined by glucometer (One Touch Ultra®, LifeScan, Inc.) and compared to vehicle control (1 ml/kg of water). Samples were collected prior to dosing (time 0) and at 15, 30, 45 and 60 minutes after dosing. The % glucose reduction values in Table 1 are values found at the C minimum, and are an average % reduction with respect to the number of times the experiment was run for each delivery agent.

TABLE 1

Percent Change in Glucose
Insulin
200 mg/kg Delivery Agent Compound; 0.5 mg/kg Insulin

| Delivery Agent Compound | % Glucose Reduction |
|---|---|
| 1 | −0.2 |
| 3 | −21.2 ± 9.7 |
| 3 | −25.7 ± 22.7 |
| 6 | −9.8 ± 30.4 |
| 7 | −8.6 ± 7.2 |
| 7 | −20.0 |
| 7 | −29.0 |
| 58 | −18.2 |
| 9 | −6.0 ± 12.9 |
| 9 | −34.6 |
| 11 | −55.8 ± 17.9 |
| 11 | −25.8 ± 8.2 |
| 12 | −40.2 ± 25.2 |
| 12 | −54.8 ± 46.3 |
| 12 | −35.3 ± 11.5 |
| 13 | −18.2 ± 17.4 |
| 14 | −13.9 ± 2.9 |
| 14 | −47.8 ± 21.2 |
| 14 | −16.9 ± 16.3 |
| 16 | −38.9 ± 32.7 |
| 17 | −36.9 ± 18.2 |
| 17 | −46.4 ± 8.1 |
| 17 | −39.9 ± 30.0 |
| 18 | −23.5 ± 29.0 |
| 18 | −22.5 ± 14.6 |
| 19 | −33.6 ± 32.4 |
| 20 | −33.9 ± 41.8 |
| 21 | −19.4 ± 6.6 |
| 22 | −3.7 ± 9.4 |
| 23 | −67.6 ± 6.4 |
| 23 | −21.0 ± 5.3 |
| 23 | −38.4 ± 26.2 |
| 24 | −10.0 ± 17.7 |
| 25 | −16.0 ± 13.4 |
| 27 | −47.6 ± 17.4 |
| 28 | −51.5 ± 27.0 |
| 28 | −28.2 ± 17.4 |
| 28 | −46.9 ± 24.9 |
| 29 | −51.0 ± 19.4 |
| 29 | −56.7 ± 20.5 |
| 29 | −69.4 ± 11.5 |
| 30 | −18.3 ± 39.0 |
| 30 | −15.2 ± 16.5 |
| 31 | −43.3 ± 16.3 |
| 31 | −37.4 ± 23.8 |
| 32 | −15.2 ± 28.9 |
| 36 | −69.1 ± 5.5 |
| 36 | −39.4 ± 34.9 |
| 36 | −51.3 ± 8.8 |
| 40 | −6.0 ± 17.5 |
| 42 | −22.1 ± 5.4 |
| 44 | −7.8 ± 16.5 |
| 45 | −6.5 ± 21.2 |
| 46 | 0.3 ± 27.7 |
| 47 | −31.2 ± 19.4 |
| 47 | −38.8 ± 8.7 |
| 48 | −43.1 ± 20.0 |
| 48 | −30.5 ± 22.9 |

TABLE 1-continued

Percent Change in Glucose
Insulin
200 mg/kg Delivery Agent Compound; 0.5 mg/kg Insulin

| Delivery Agent Compound | % Glucose Reduction |
|---|---|
| 48 | −32.8 ± 16.4 |
| 49 | −34.6 ± 11.5 |
| 49 | −17.2 ± 23.7 |
| 50 | −15.8 ± 10.6 |
| 51 | −24.9 ± 6.2 |
| 52 | −60.3 ± 18.9 |
| 52 | −32.6 ± 22.6 |
| 53 | −14.8 ± 7.0 |
| 54 | −37.4 ± 26.0 |
| 55 | −20.9 ± 17.5 |
| 56 | −4.5 ± 11.1 |
| 57 | −11.0 ± 15.7 |

0.5 mg/kg of Insulin and 25-100 mg/kg of delivery agent compound (particular amount shown in Table 2 below) was administered to male Sprague-Dawley rats with an average weight of about 225-250 grams. The purpose of this test was to ascertain the dose response of the delivery agent compound. Glucose reduction was determined as set forth in connection with the data in Table 1.

TABLE 2

Dose Response of Delivery Agent Compounds 2, 5, 6 and 8
Delivery Agent Dose Response:
Insulin 0.5 mg/kg

| Delivery Agent Compound | Amount of Delivery Agent Compound (mg/kg) | % Glucose Reduction |
|---|---|---|
| 2 | 25 | −10.0 |
| 5 | 50 | −13.5 |
| 5 | 100 | −18.2 |
| 6 | 100 | −19.2 |
| 6 | 50 | −15.8 |
| 8 | 50 | −30.5 |
| 8 | 25 | −9.7 |

Insulin Titrations were performed with Delivery Agent 29 in order to gauge the effect of varying dosages of insulin. The results are shown below in Table 3:

TABLE 3

Insulin Dose Titrations of Delivery Agent Compounds
Insulin Titrations:
Delivery Agent 200 mg/kg

| Delivery Agent Compound | Dose of Insulin (mg/kg) | % Glucose Reduction |
|---|---|---|
| 29 | 0.50 | −30.8 |
| 29 | 0.25 | −31.4 |
| 29 | 0.00 | −6.8 |

Example 68—Oral and Intracolonic Delivery of Heparin to Male Sprague-Dawley Rats Oral gavage and/or intracolonic (IC) dosing solutions containing delivery agent compound and heparin sodium USP were prepared in 25% aqueous propylene glycol. Either the sodium salt of the delivery agent compound was used or the free acid was converted to the sodium salt with one equivalent of sodium hydroxide. The delivery agent compound and heparin (about 166-182 IU/mg) were mixed by vortex as dry powders. This dry mixture was dissolved in 25% v/v aqueous propylene glycol, vortexed, and placed in a sonicator (about 37° C.). The pH was adjusted to about 7 (6.5-8.5) with aqueous NaOH (2N). The dosing solution was sonicated to produce a clear solution. The final volume was adjusted to about 3.0 ml. The final delivery agent compound dose, and heparin dose are listed in Table 4.

Male Sprague-Dawley rats weighing between about 275-350 g were fasted for 24 hours and anesthetized with ketamine hydrochloride (88 mg/kg) intramuscularly immediately prior to dosing and again as needed to maintain anesthesia. A dosing group of five animals were administered one of the dosing solutions. For oral gavage dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

For intracolonic (IC) dosing, a 7.5 cm, 8 French Rusch catheter was adapted to a 1 ml syringe with a pipette tip. The dosing catheter was inserted into the colon through the anus until the tube was no longer visible. The dosing solution was expressed slowly into the colon by pressing the syringe plunger.

Citrated blood samples were collected by cardiac puncture following the administration of ketamine (88 mg/kg), typically at 0.25, 0.5, 1.0 and 1.5 hours after dosing. Heparin absorption was verified by an increase in clotting time measured by the activated partial thromboplastin time (APTT) according to the method of Henry, J. B., Clinical Diagnosis and Management by Laboratory Methods, Philadelphia, Pa., W.B. Saunders (1979), which is hereby incorporated by reference. Previous studies indicated baseline values of about 20 seconds. Results from the animals in each group were averaged for each time points and the highest of these averages (i.e. mean peak APTT) is reported.

Figure 2:
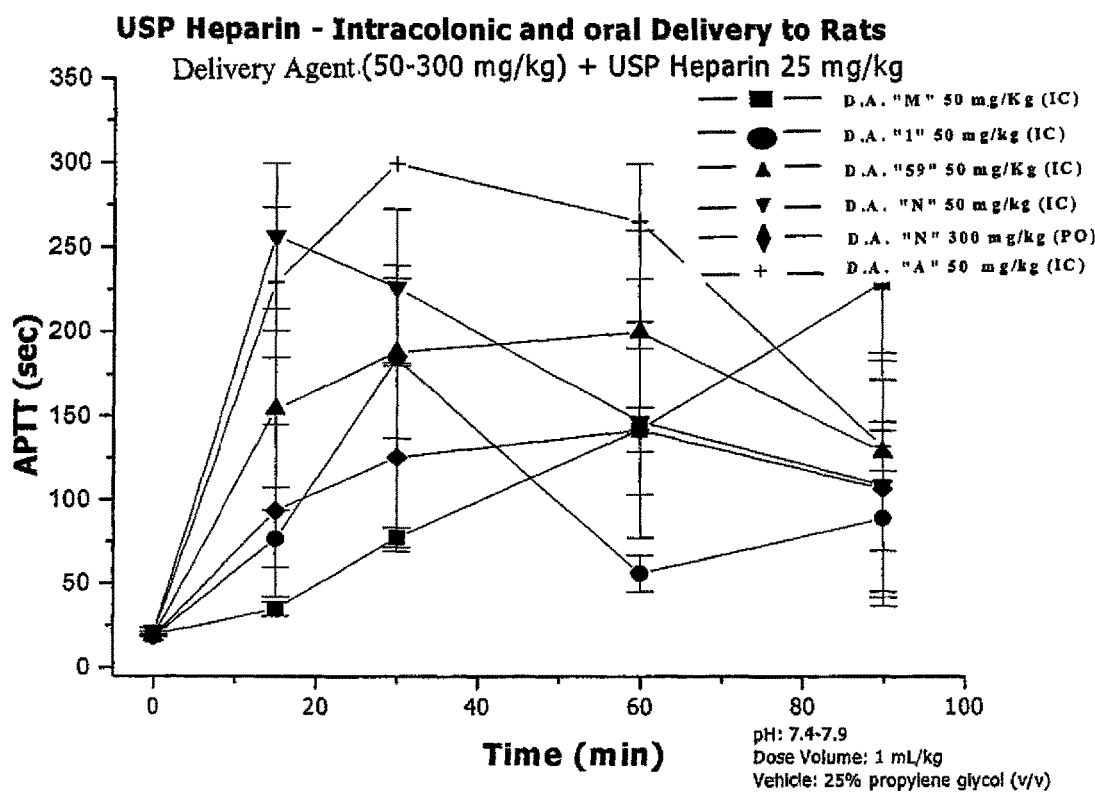
Figure 3:
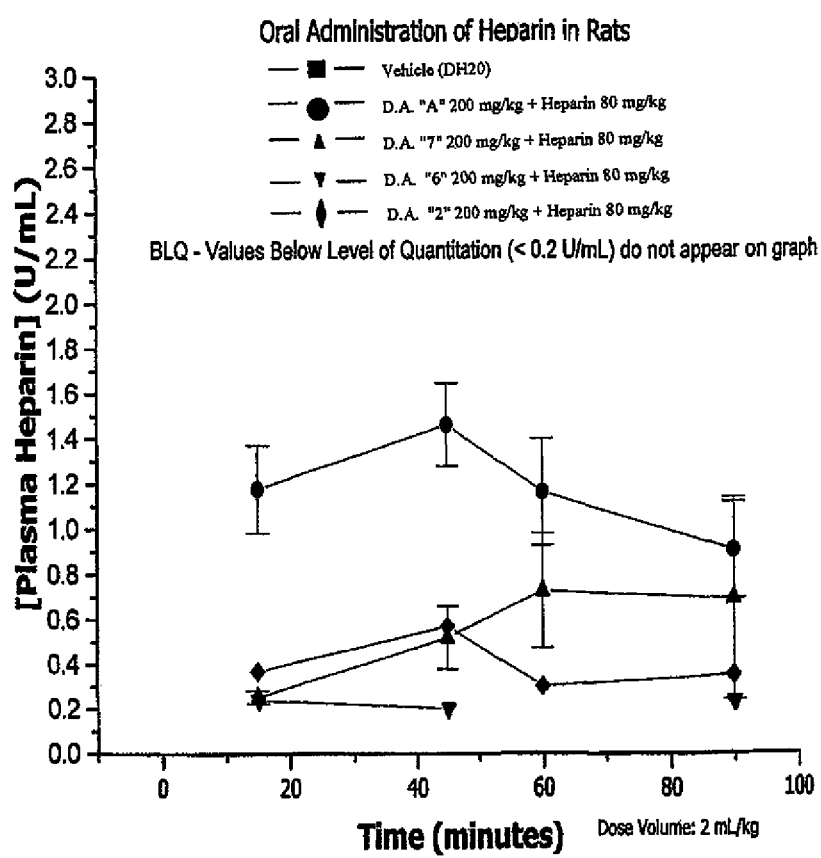
FIG. 3 is a graph of plasma heparin concentrations obtained after administration of heparin with delivery agents 2, 6 and 7 to male rats over 90 minutes.

The oral and intracolonic APTT results and plasma heparin concentrations for delivery agents 1, 2, 6, 7, 11, 35 and 59 are shown in FIG. 1-3. The following delivery agents were administered as positive controls:

| Delivery Agent Structure | Notation in FIG. |
|---|---|
| [structure] | D.A. "A" |
| [structure] | D.A. "J" |
| [structure] | D.A. "K" |
| [structure] | D.A. "L" |
| [structure] | D.A. "M" |
| [structure] | D.A. "N" |

TABLE 4

Intracolonic delivery of Heparin
Intracolonic:
Delivery Agent 50 mg/kg; USP Heparin 25 mg/kg

| Delivery Agent | APTT (seconds) | Tmax (Minutes) |
| --- | --- | --- |
| 11 | 300.0 | 30.0 |
| 35 | 100.0 | 30.0 |
| 1 | 180 | 30 |

TABLE 5

Oral delivery of Heparin
Oral:
Delivery Agent 200 mg/kg; Heparin 80 mg/kg

| Delivery Agent | [Plasma Heparin] (U/mL) | Tmax (Minutes) |
| --- | --- | --- |
| 2 | 0.5 | 45 |
| 6 | 0.2 | 15 |
| 7 | 0.7 | 60 |

Example 69—Oral Delivery of Recombinant Human Growth Hormone (rhGH) to Male Sprague-Dawley Rats Oral gavage dosing solutions of delivery agent compound and rhGH in phosphate buffer were prepared by mixing. A solution of the delivery agent compound was made either with the sodium salt of the delivery agent compound or by converting the free acid to its sodium salt. A solution of the delivery agent compound was prepared in phosphate buffer and stirred, adding one equivalent of sodium hydroxide (1.0 N) when making the sodium salt. The final dosing solutions were prepared by mixing the delivery agent compound solution with an rhGH stock solution (15 mg rhGH/ml glycine and 3.39 mg dibasic sodium phosphate, then diluted with 2% glycerol) with rhGH obtained from Eli Lilly and diluting to the desired volume (usually 3.0 ml). The pH was adjusted, if necessary, to between about 7 and 8.8. The delivery agent compounds and rhGH dose amounts are listed in Table 6.

Male Sprague-Dawley rats weighing about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with the dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery at time=15, 30, 45, 60 and 90 minutes. The five samples from each time period were pooled. Serum rhGH concentrations were quantified by an rhGH immunoassay test kit. Previous studies indicated baseline values of about zero. The maximum concentration at Tmax for each group tested with rhGH is listed.

TABLE 6

Oral delivery of rhGH
Oral:
Delivery Agent 200 mg/kg; rhGH 3 mg/kg

| Delivery Agent | Serum Level (ng/mL) | Tmax (Minutes) |
| --- | --- | --- |
| 11 | 5 | 15 |
| 11 | 1 | 60 |
| 11 | 1 | 15 |

Figure 4:
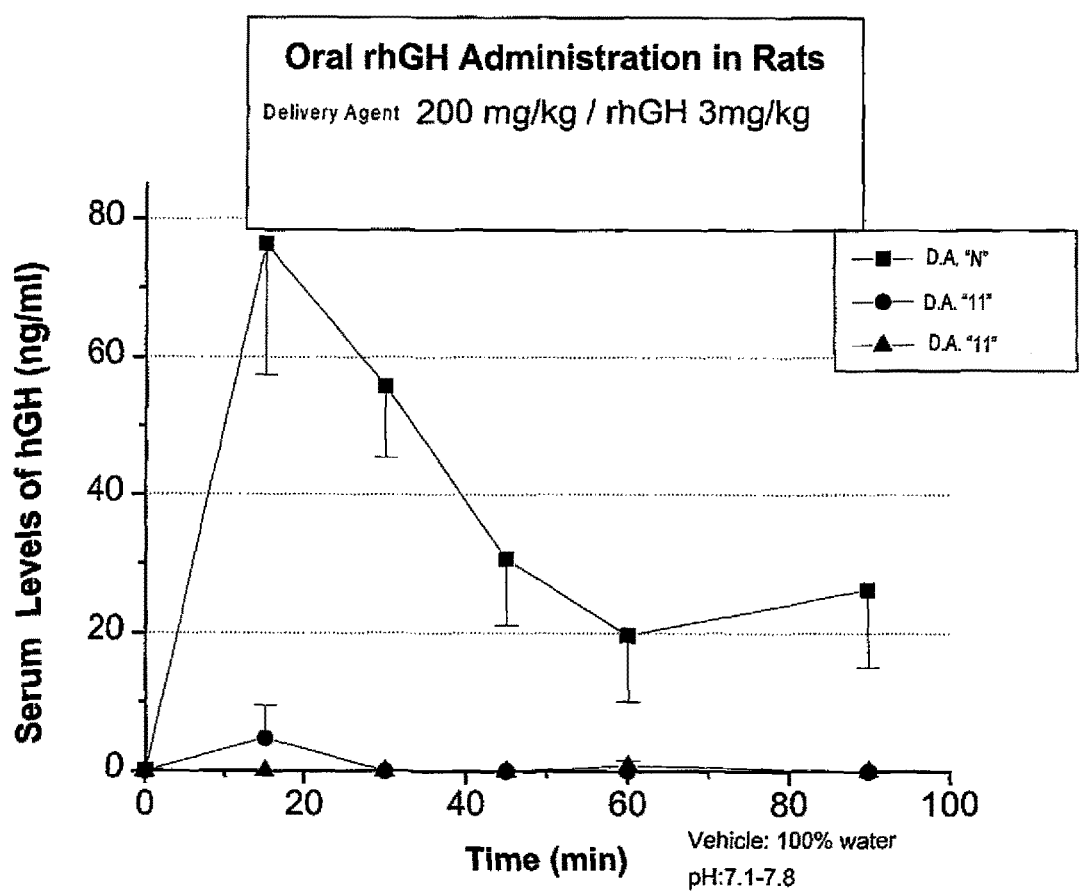
FIGS. 4 and 5 are graphs of serum rhGH levels in male rats after administration of rhGH with delivery agent 11 to male rats over 90 minutes.
Figure 5:
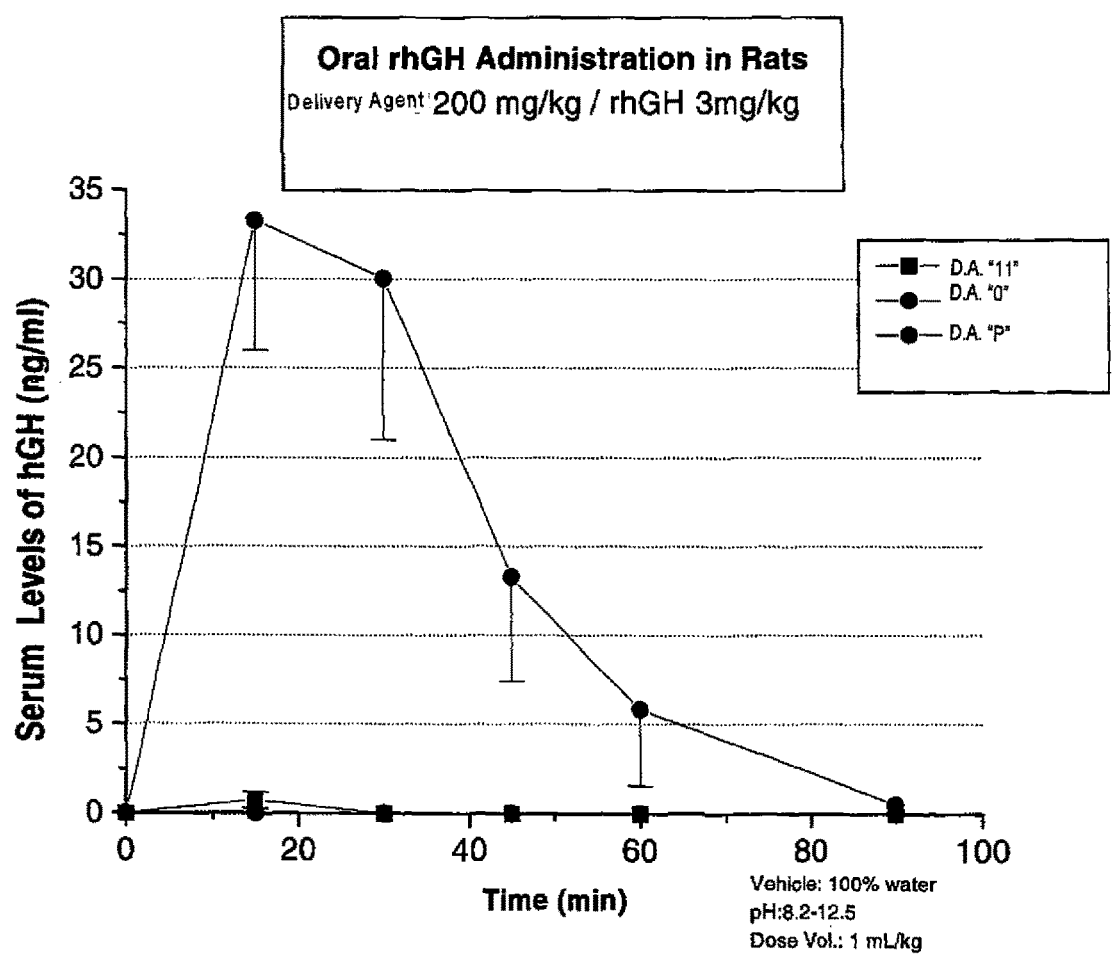

Average serum hGH concentrations over 90 minutes for delivery agent 11 is shown in FIGS. 4 and 5. The following delivery agents were administered as positive controls:

| Delivery Agent Structure | Notation in FIG. |
| --- | --- |
| 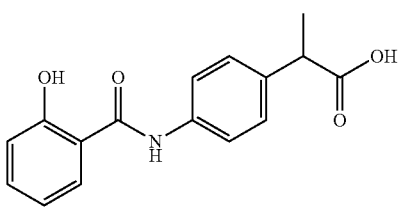 [SMILES: CC(C(=O)O)c1ccc(NC(=O)c2ccccc2O)cc1] | D.A. "N" |
| 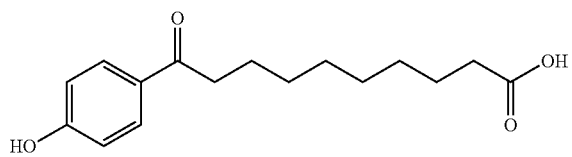 [SMILES: O=C(O)CCCCCCCCC(=O)c1ccc(O)cc1] | D.A. "O" |
| 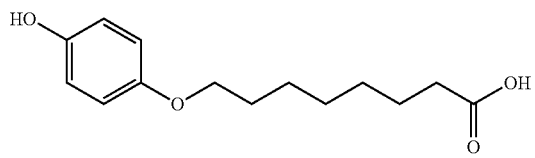 [SMILES: O=C(O)CCCCCCCOc1ccc(O)cc1] | D.A. "P" |

Example 70—Oral Delivery of Luteinizing Hormone-Releasing Hormone (LHRH) to Male Sprague-Dawley Rats Oral gavage dosing solutions of delivery agent compound and LHRH in phosphate buffer were prepared by mixing. A solution of the delivery agent compound was made either with the sodium salt of the delivery agent compound or by converting the free acid to its sodium salt. A solution of the delivery agent compound was prepared in phosphate buffer and stirred, adding one equivalent of sodium hydroxide (1.0 N) when making the sodium salt. The final dosing solutions were prepared by mixing the delivery agent compound solution with a LHRH stock solution (2.75 ml with a concentration of 20 mg/ml in aqueous solution). The pH was adjusted, if necessary, to between about 7 and 8.8. The delivery agent compounds and LHRH dose amounts are listed in Table 7.

Male Sprague-Dawley rats weighing between about 250-300 g were fasted for 24 hours. A dosing group of five animals was administered one of the dosing solutions. An 11 cm Rusch 8 French catheter was adapted to a 1 ml syringe with a pipette tip. The syringe was filled with the dosing solution by drawing the solution through the catheter, which was then wiped dry. The catheter was placed down the esophagus leaving 1 cm of tubing past the incisors. The dosing solution was administered by pressing the syringe plunger.

Figure 6:
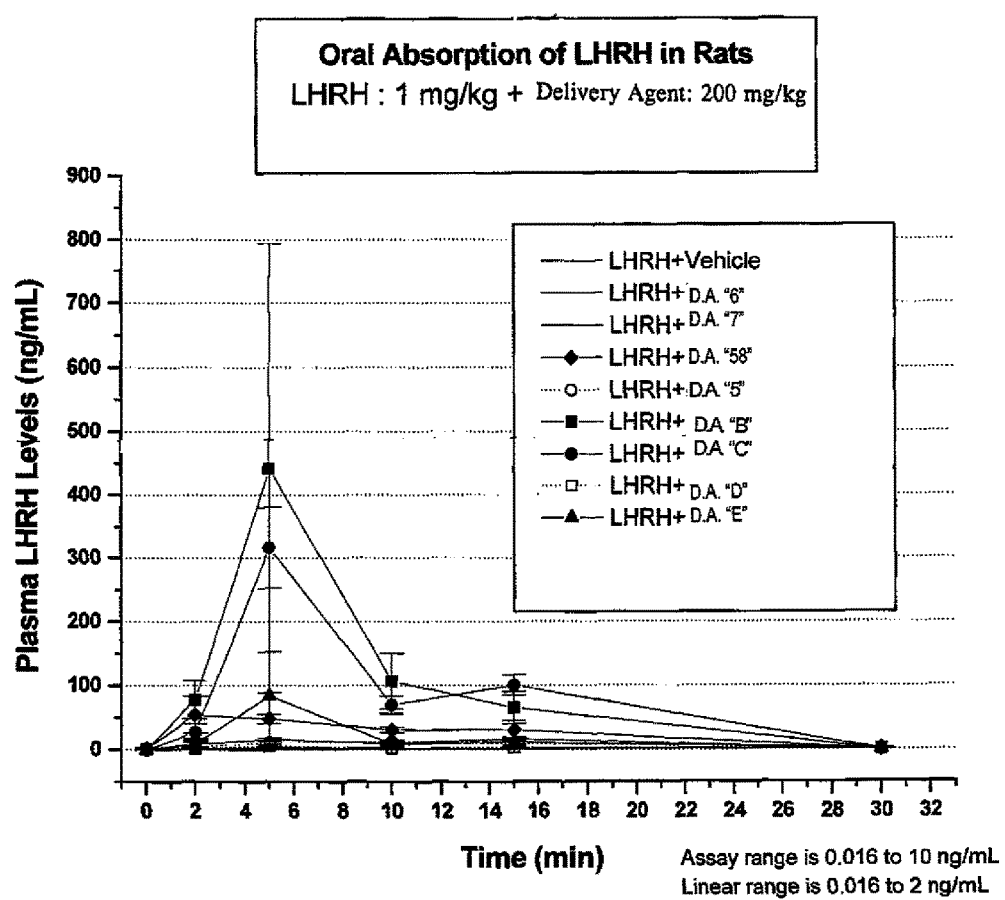
FIG. 6 is a graph of serum LHRH concentrations after administration of LHRH with delivery agents 5, 6, 7 and 58 to male rats over 30 minutes.

Blood samples were collected through retroorbital bleeding of approximately 0.4 ml of blood volume using EDTA tubes at time=0 (pre-dose), 2, 10, 15 and 30 minutes. The five samples from each time period were pooled. Previous studies indicated baseline values of about zero. The maximum absorption at the Tmax is reported below in Table 7. Results for delivery agents 5, 6, 7 and 58 are also shown in FIG. 9. As controls, 4-(3-methyl phenoxy) butyric acid (D.A. "B"), the mesylate salt of (4-(8-(2-hydroxyphenoxy) octyl) morpholine (D.A. "C"), 4-(4-(2-hydroxyphenoxy) butyl) morpholine (D.A. "D"), and 4-(6-(2-hydroxyphenoxy)hexyl) morpholine (D.A. "E") were also administered according to the same protocol and their results are also shown in FIG. 6.

TABLE 7

Oral delivery of LHRH
Oral Absorption of LHRH in Rats
Delivery Agent: 200 mg/kg; LHRH: 1 mg/kg

| Delivery Agent | Plasma LHRH concentration (ng/mL) | Tmax (Minutes) |
| --- | --- | --- |
| 1 | 5 | 5 |
| 3 | 33 | 5 |
| 4 | 2 | 5 |
| 5 | 5 | 5 |
| 6 | 0 | 5 |
| 7 | 0 | 5 |

Example 71—Oral Delivery of Caspofungin Acetate to Male Sprague-Dawley Rats

Oral gavage dosing solutions of delivery agent compound and caspofungin acetate (Merck & Co., Whitehouse Station, N.J.) in phosphate buffer were prepared by mixing. A solution of the delivery agent compound was made either with the sodium salt of the delivery agent compound or by converting the free acid to its sodium salt. A solution of the delivery agent compound was prepared in phosphate buffer and stirred, adding one equivalent of sodium hydroxide (1.0 N) when making the sodium salt. The final dosing solutions were prepared by mixing the delivery agent compound solution with a caspofungin acetate stock solution (2.5 ml with a concentration of 100 mg/ml in aqueous solution). The pH was adjusted, if necessary, to between about 7 and 8.8. The delivery agent compounds and caspofungin acetate dose amounts are listed in Table 8.

Male Sprague-Dawley rats weighing between about 250-300 g were fasted for 24 hours. A dosing group of five animals was administered one of the dosing solutions. An 11 cm Rusch 8 French catheter was adapted to a 1 ml syringe with a pipette tip. The syringe was filled with the dosing solution by drawing the solution through the catheter, which was then wiped dry. The catheter was placed down the esophagus leaving 1 cm of tubing past the incisors. The dosing solution was administered by pressing the syringe plunger.

Blood samples were collected through retroorbital bleeding at time=0 (pre-dose), 15, 30, 60, 240, and 480 minutes. The five samples from each time period were pooled. Previous studies indicated baseline values of about zero. The maximum concentration at the Tmax is reported.

TABLE 8

Oral delivery of caspofungin acetate
Oral caspofungin acetate:
Delivery Agent 200 mg/kg; caspofungin acetate: 25 mg/kg

| Delivery Agent | plasma caspofungin acetate concentration (ng/mL) | Tmax (Minutes) |
| --- | --- | --- |
| 14 | 190 | 60 |

Figure 7:
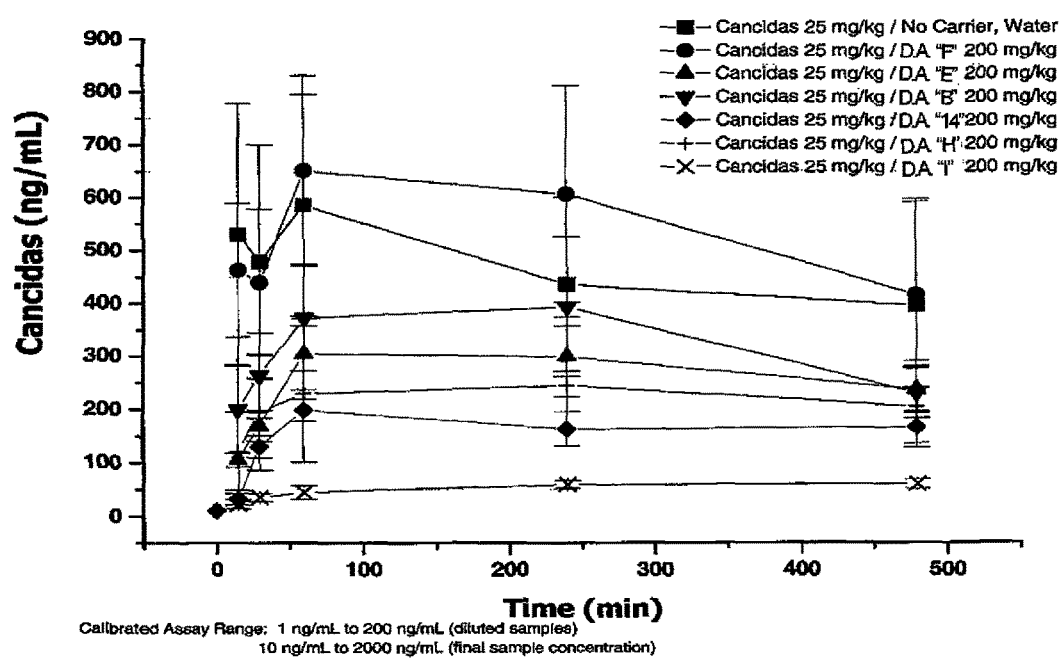
FIG. 7 is a graph of serum caspofungin acetate concentrations after administration of caspofungin acetate after administration of caspofungin acetate with delivery agent 14 over about 500 minutes

The results for delivery agent 14 is also shown in FIG. 10. The delivery agents N-6-2-hydroxy-5-chlorobenzoyl amino hexanoic acid (D.A. "F"), 6-(2-methylformylphenoxy) hexanoic acid (D.A. "E"), 4-(3-methylphenoxy) butyric acid (D.A. "B"), 3-(3-fluoro) propionic acid (D.A. "H"), and 5-phenyl pentanoic acid (D.A. "I") were also administered as controls according to the same protocol and their results are shown in FIG. 7.

The above-mentioned patents, applications, test methods, and publications are hereby incorporated by reference in their entirety.

The present invention has been described in details with particular reference to the preferred embodiments thereof, but it will be understood that many variations and modifications of the present invention suggest themselves to those skilled in the art in light of the above detailed description. All such obvious variations and modifications can be affected without departing the spirit and scope of the appended claims of the present invention.

The invention claimed is:
1. A compound selected from:

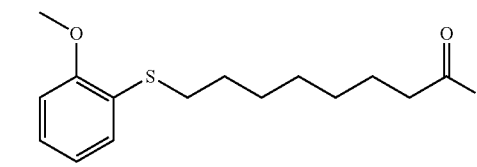

Compound 1

8-(2-Methoxy-phenylsulfanyl)-octanoic acid

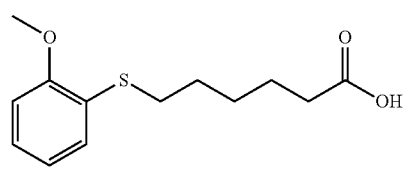

Compound 3

6-(2-Methoxy-phenylsulfanyl)-hexanoic acid

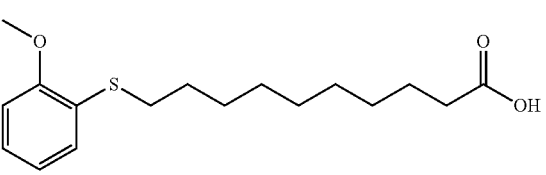

Compound 4

10-(2-Methoxy-phenylsulfanyl)-decanoic acid

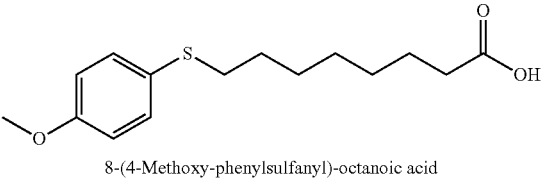

Compound 10

8-(4-Methoxy-phenylsulfanyl)-octanoic acid

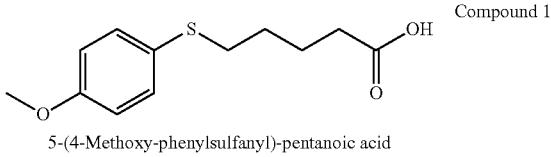

Compound 14

5-(4-Methoxy-phenylsulfanyl)-pentanoic acid

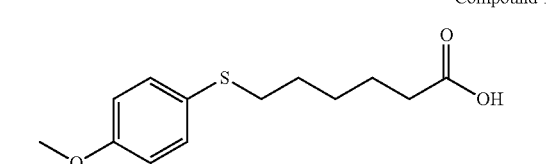

Compound 15

6-(4-Methoxy-phenylsulfanyl)-hexanoic acid

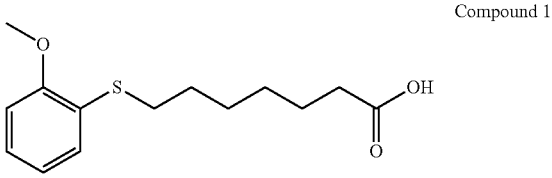

Compound 16

7-(2-Methoxy-phenylsulfanyl)-heptanoic acid

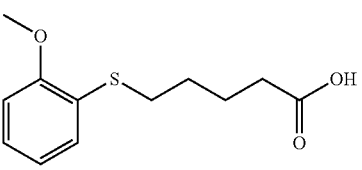

Compound 19

5-(2-Methoxy-phenylsulfanyl)-pentanoic acid

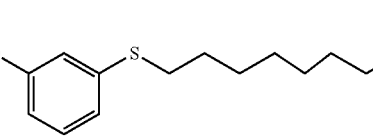

Compound 20

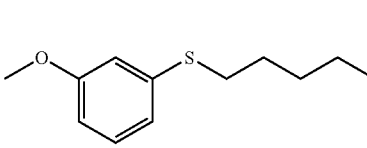

Compound 21

6-(3-Methoxy-phenylsulfanyl)-hexanoic acid

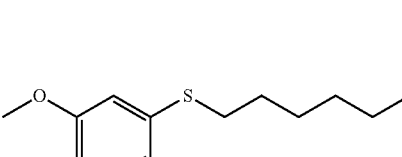

Compound 22

8-(3-Methoxy-phenylsulfanyl)-octanoic acid

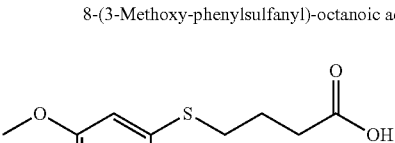

Compound 27

4-(3-Methoxy-phenylsulfanyl)-butyric acid

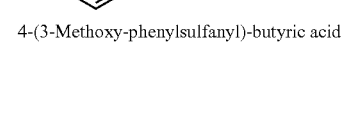

Compound 60

[4-(2-Methoxy-phenylsulfanylmethyl)-phenyl]-acetic acid

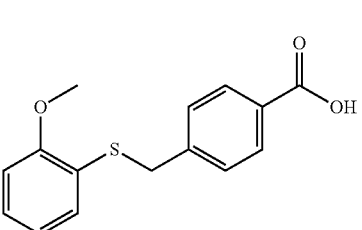

Compound 61

4-(2-Methoxy-phenylsulfanylmethyl)-benzoic acid

-continued

Compound 65

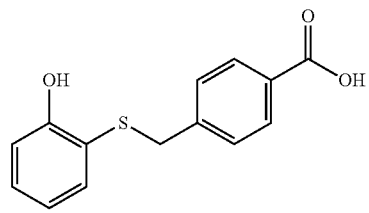

4-(2-Hydroxy-phenylsulfanylmethyl)-benzoic acid

Compound 66

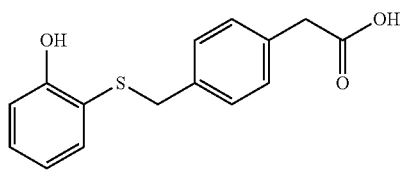

4-(2-Hydroxy-phenylsulfanylmethyl)-phenyl]-acetic acid and pharmaceutically acceptable salts thereof.

2. A pharmaceutical composition comprising:
   (A) a biologically active agent; and
   (B) a delivery agent compound of Formula I, or a pharmaceutically acceptable salt thereof Formula I

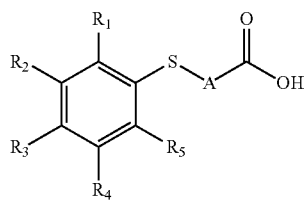

wherein
  A is a branched or unbranched $C_1$-$C_{13}$ alkylene, $C_3$-$C_{13}$ arylene group, or a $C_3$-$C_{13}$ alkyl(arylene) group, and
  $R_1$-$R_5$ are independently hydrogen, $C_1$-$C_4$ alkyl, $C_1$-$C_4$ alkoxy, $C_2$-$C_4$ alkenyl, halogen or hydroxy, in which at least one of $R_1$-$R_5$ is methoxy.

3. A pharmaceutical composition comprising:
   (A) a biologically active agent; and
   (B) a delivery agent compound selected from Compound 1

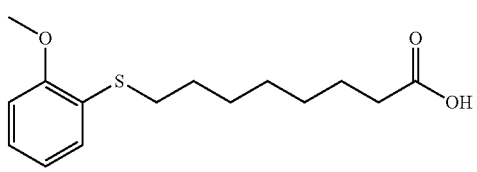

8-(2-Methoxy-phenylsulfanyl)-octanoic acid

Compound 3

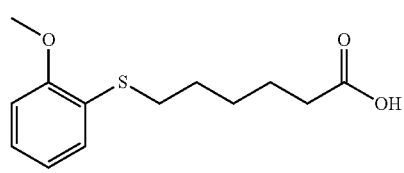

6-(2-Methoxy-phenylsulfanyl)-hexanoic acid

-continued

Compound 4

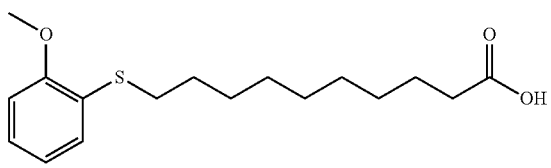

10-(2-Methoxy-phenylsulfanyl)-decanoic acid

Compound 10

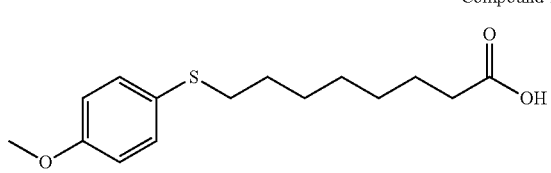

8-(4-Methoxy-phenylsulfanyl)-octanoic acid

Compound 13

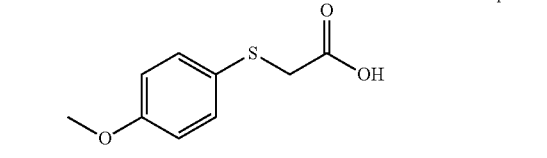

(4-Methoxy-phenylsulfanyl)-acetic acid

Compound 14

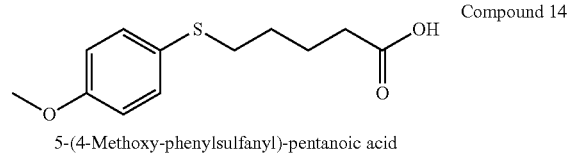

5-(4-Methoxy-phenylsulfanyl)-pentanoic acid

Compound 15

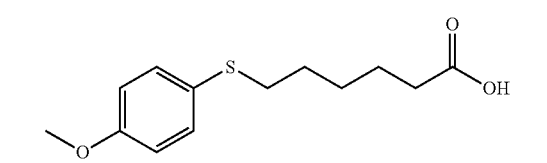

6-(4-Methoxy-phenylsulfanyl)-hexanoic acid

Compound 16

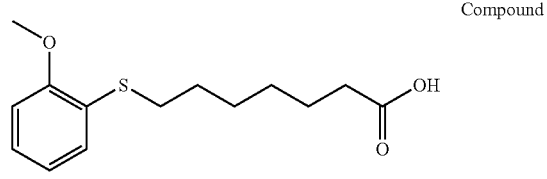

7-(2-Methoxy-phenylsulfanyl)-heptanoic acid

Compound 17

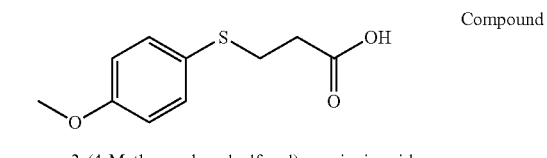

4-(4-Methoxy-phenylsulfanyl)-butyric acid

Compound 18

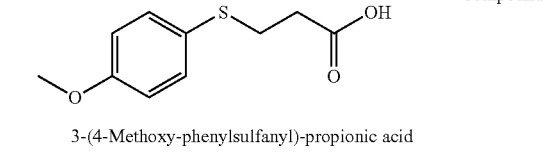

3-(4-Methoxy-phenylsulfanyl)-propionic acid

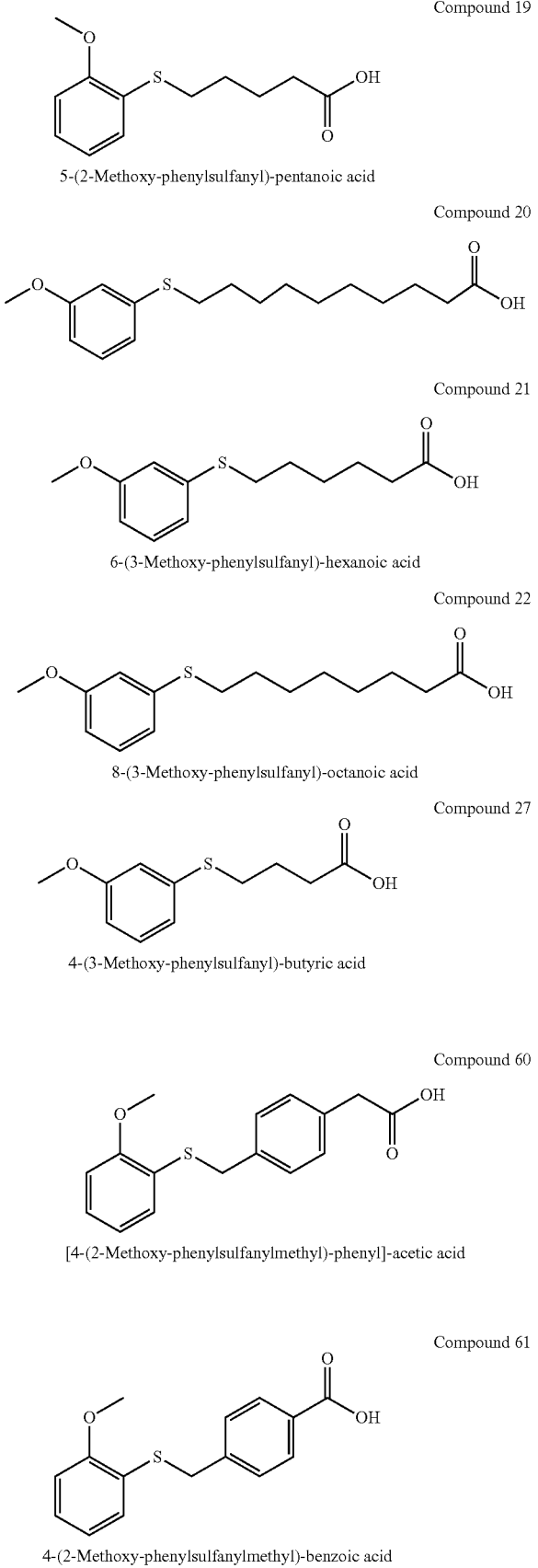

and pharmaceutically acceptable salts thereof.

4. The pharmaceutical composition of claim 2 or claim 3, wherein the biologically active agent is a protein, polypeptide, peptide, hormone, polysaccharide, mucopolysaccharide, carbohydrate, or lipid.

5. The pharmaceutical composition of claim 4, wherein the biologically active agent is selected from: BIBN-4096BS, growth hormones, human growth hormones, recombinant human growth hormones (rhGH), bovine growth hormones, porcine growth hormones, growth hormone releasing hormones, growth hormone releasing factor, glucagon, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine (DFO), parathyroid hormone (PTH), fragments of PTH, glucagon-like peptide 1 (GLP-1), antimicrobials, antifungal agents, vitamins; analogs, fragments, mimetics and polyethylene glycol (PEG)-modified derivatives of these compounds; gallium or gallium salts; glucagons; zanamivir, sumatriptan, almotriptan, naratriptan, rizatriptan, frovatriptan, eletriptan, caspofungin acetate, CPHPC, RNAi and any combination thereof.

6. The pharmaceutical composition of claim 5, wherein the biologically active agent is selected from insulin, leutinizing-hormone releasing hormone, heparin, recombinant human growth hormone, glucagon, caspofungin acetate, calcitonin, PTH, zanamivir, erythropoietin, analogs, fragments, mimetics and polyethylene glycol (PEG)-modified derivatives of these compounds; and any combination thereof.

7. The pharmaceutical composition of claim 5, wherein the biologically active agent comprises insulin.

8. A dosage unit form comprising:
(A) a pharmaceutical composition of claim 2 or claim 3;
(B) a biologically active agent; and
(C) (a) an excipient,
  (b) a diluents,
  (c) a disintegrant,
  (d) a lubricant,
  (e) a plasticizer,
  (f) a colorant,
  (g) a dosing vehicle, or
  (h) any combination thereof.

9. The dosage unit form of claim 8, wherein the biologically active agent is a protein, polypeptide, peptide, hormone, polysaccharide, mucopolysaccharide, carbohydrate, or lipid.

10. The dosage unit form of claim 9, wherein the biologically active agent is selected from: argatroban, BIBN-4096BS, growth hormones, human growth hormones (hGH), recombinant human growth hormones (rhGH), bovine growth hormones, porcine growth hormones, growth hormone releasing hormones, growth hormone releasing factor, interferons, glucagon, α-interferon, β-interferon, γ-interferon, interleukin-1, interleukin-2, insulin, porcine insulin, bovine insulin, human insulin, human recombinant insulin, insulin-like growth factor, insulin-like growth factor-1, heparin, un fractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, parathyroid hormone, fragments of PTH, glucagon-like peptide 1 (GLP-1), anti-microbials, anti-fungal agents, vitamins; analogs, fragments, mimetics and polyethylene glycol-modified derivatives of these compounds; gallium or gallium salts; glucagons, zanamivir, sumatriptan, almotriptan, naratriptan, rizatriptan, frovatriptan, eletriptan, capsofungin acetate, CPHPC, RNAi and any combination thereof.

11. The dosage unit form of claim 10, wherein the biologically active agent is insulin, Leutenizing-hormone releasing hormone, heparin, Recombinant Human Growth Hormone, glucagon, caspofungin acetate, calcitonin, PTH, zanamivir, erythropoietin or a combination thereof.

12. The dosage unit form of claim 9, wherein the active agent is insulin.

13. The dosage unit form of claim 9, wherein the active agent is glucagon.

14. The dosage unit form of claim 8, wherein the dosage unit form is a tablet, a capsule, a powder, or a liquid.

15. The dosage unit form of claim 8, wherein the dosing vehicle is a liquid selected from water, 1,2-propane diol, ethanol, and any combination thereof.

16. A method for administering a biologically-active agent to an animal in need of the agent, the method comprising administering orally to the animal a pharmaceutical composition of any one of claims 2-3.

17. A method for preparing a pharmaceutical composition comprising mixing:
(A) a biologically active agent;
(B) at least one compound of claim 1; and
(C) optionally, a dosing vehicle
wherein the ratio of compound (B) to biologically active agent (A) ranges from about 400:1 to about 25:1.

18. A pharmaceutical composition comprising:
(A) a biologically active agent; and
(B) a compound of Formula I, or a pharmaceutically acceptable salt thereof

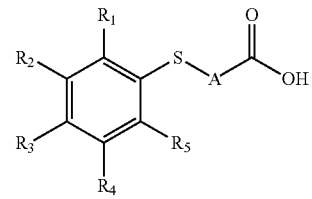

Formula I wherein
  A is a branched or unbranched $C_1$-$C_{13}$ alkylene, $C_3$-$C_{13}$ arylene group, or a $C_3$-$C_{13}$ alkyl(arylene) group,
  $R_1$-$R_5$ are independently hydrogen, $C_1$-$C_4$ alkyl, $C_1$-$C_4$ alkoxy, $C_2$-$C_4$ alkenyl, halogen or hydroxy, in which at least one of $R_1$-$R_5$ is methoxy,
wherein the ratio of compound of Formula (I) to biologically active agent ranges from about 400:1 to about 25:1.

19. The pharmaceutical composition of claim 2, wherein the ratio of delivery agent to biologically active agent is about 2:1, about 2.5:1, about 8:1, about 50:1, about 66.7:1, about 100:1, about 200:1, or about 500:1.

20. The method of claim 16, wherein the ratio of delivery agent to biologically active agent is about 2:1, about 2.5:1, about 8:1, about 50:1, about 66.7:1, about 100:1, about 200:1, or about 500:1.

21. The pharmaceutical composition of claim 2, wherein the ratio of delivery agent compound to biologically active agent ranges from about 400:1 to about 25:1.

22. The pharmaceutical composition of claim 3, wherein the ratio of delivery agent compound to biologically active agent ranges from about 400:1 to about 25:1.

23. The pharmaceutical composition of claim 3, wherein the ratio of delivery agent to biologically active agent is about 2:1, about 2.5:1, about 8:1, about 50:1, about 66.7:1, about 100:1, about 200:1, or about 500:1.

* * * * *